(12) United States Patent
Rahbari et al.

(10) Patent No.: US 12,702,760 B2
(45) Date of Patent: Aug. 11, 2026

(54) CASSETTE FOR AN AUTOINJECTOR AND RELATED METHODS

(71) Applicant: AMGEN INC., Thousand Oaks, CA (US)

(72) Inventors: Azita Rahbari, Westlake Village, CA (US); Sunitha Dasoju, Ventura, CA (US); Angelo Tosarini, Milan (IT); Antonio Antonini, Milan (IT); Julian Jazayeri, Woodland Hills, CA (US); Harpreet Sachar, Newbury Park, CA (US); Andrew Coles, Thousand Oaks, CA (US); Desheng Yin, Thousand Oaks, CA (US); Alireza Ashani, Woodland Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 1126 days.

(21) Appl. No.: 17/437,615

(22) PCT Filed: Apr. 10, 2020

(86) PCT No.: PCT/US2020/027576
§ 371 (c)(1),
(2) Date: Sep. 9, 2021

(87) PCT Pub. No.: WO2020/214492
PCT Pub. Date: Oct. 22, 2020

(65) Prior Publication Data

US 2022/0184318 A1 Jun. 16, 2022

Related U.S. Application Data

(60) Provisional application No. 62/835,249, filed on Apr. 17, 2019.

(51) Int. Cl.
*A61M 5/315* (2006.01)
*A61M 5/24* (2006.01)
*A61M 5/32* (2006.01)

(52) U.S. Cl.
CPC ...... *A61M 5/31515* (2013.01); *A61M 5/2422* (2013.01); *A61M 5/31505* (2013.01); *A61M 5/3202* (2013.01); *A61M 2207/00* (2013.01)

(58) Field of Classification Search
CPC ............ A61M 5/31515; A61M 5/2422; A61M 5/31505; A61M 5/3202; A61M 2207/00;
(Continued)

(56) References Cited

U.S. PATENT DOCUMENTS

2009/0292246 A1 11/2009 Slate et al.
2010/0022955 A1 1/2010 Slate et al.
(Continued)

FOREIGN PATENT DOCUMENTS

WO WO-2009/143255 A1 11/2009
WO WO-2012145685 A1 10/2012
WO WO-2014020000 A1 2/2014
WO WO-2015110532 A1 7/2015

OTHER PUBLICATIONS

Third Party Observation for European Application No. EP20200722914 from the European Patent Organization, Applicant: Amgen Inc., mailing date Dec. 23, 2024.
(Continued)

*Primary Examiner* — Michael J Tsai
*Assistant Examiner* — Kathleen Paige Farrell
(74) *Attorney, Agent, or Firm* — MARSHALL, GERSTEIN & BORUN LLP

(57) ABSTRACT

A cassette for a drug delivery device is described that includes a sleeve, a syringe having a barrel disposed in the sleeve, and a plunger-stopper slidably disposed within the barrel. An end cap is adapted to couple to the sleeve to
(Continued)

secure the syringe in the sleeve. The cassette further includes a spacer that is sized to be slidably moved within the barrel and the spacer is disposed distal to the plunger-stopper to be engaged by a plunger rod to slide within the barrel and engage the plunger-stopper. In some forms, the spacer can be coupled to the end cap.

22 Claims, 18 Drawing Sheets

(58) Field of Classification Search
CPC .. A61M 2005/2006; A61M 2005/2026; A61M 2005/206; A61M 2005/208; A61M 2205/12; A61M 2205/19; A61M 5/20
See application file for complete search history.

(56) References Cited

U.S. PATENT DOCUMENTS

2015/0045729 A1* 2/2015 Denzer et al. .......... A61M 5/20
2017/0000955 A1* 1/2017 Mcloughlin et al. ... A61M 5/20
2017/0354781 A1* 12/2017 Cronenberg et al. ........................ A61M 5/31545

OTHER PUBLICATIONS

International Search Report for International Application No. PCT/US2020/027576, Jul. 8, 2020.
Written Opinion of the International Searching Authority for International Application No. PCT/US2020/027576, Jul. 8, 2020.

* cited by examiner 251
250
253
253
254
236
230
260
266
224
220
222A
222
216
210
214A
214
240
200

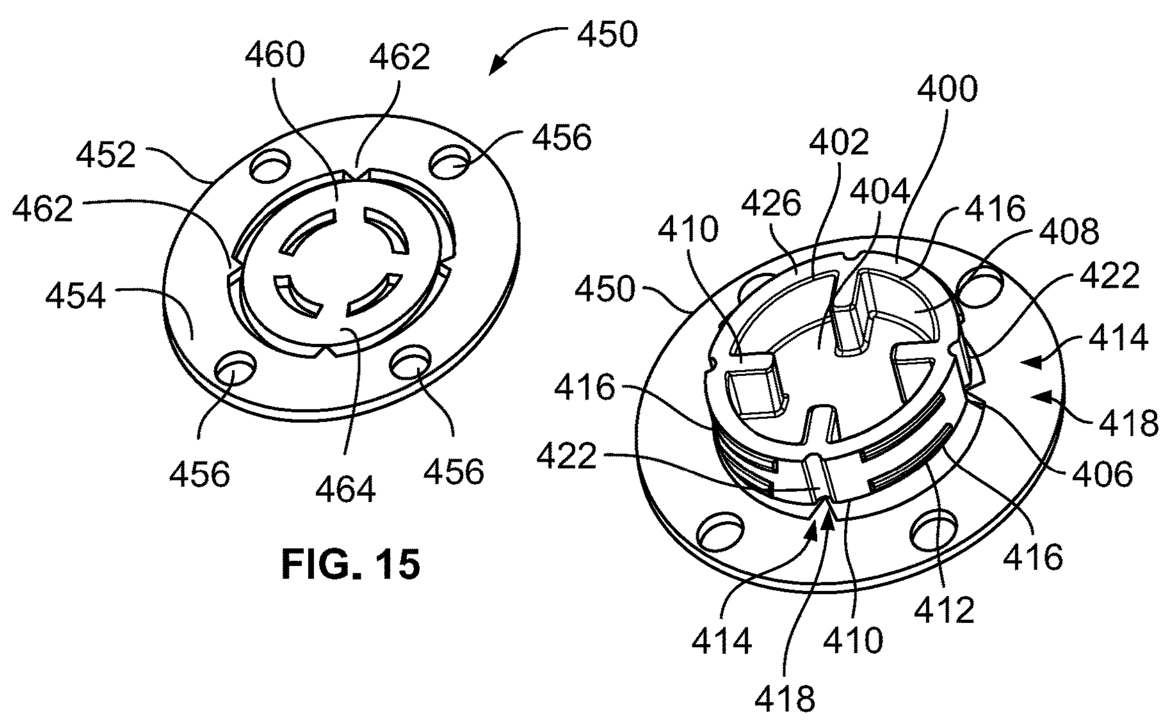
FIG. 15
FIG. 16
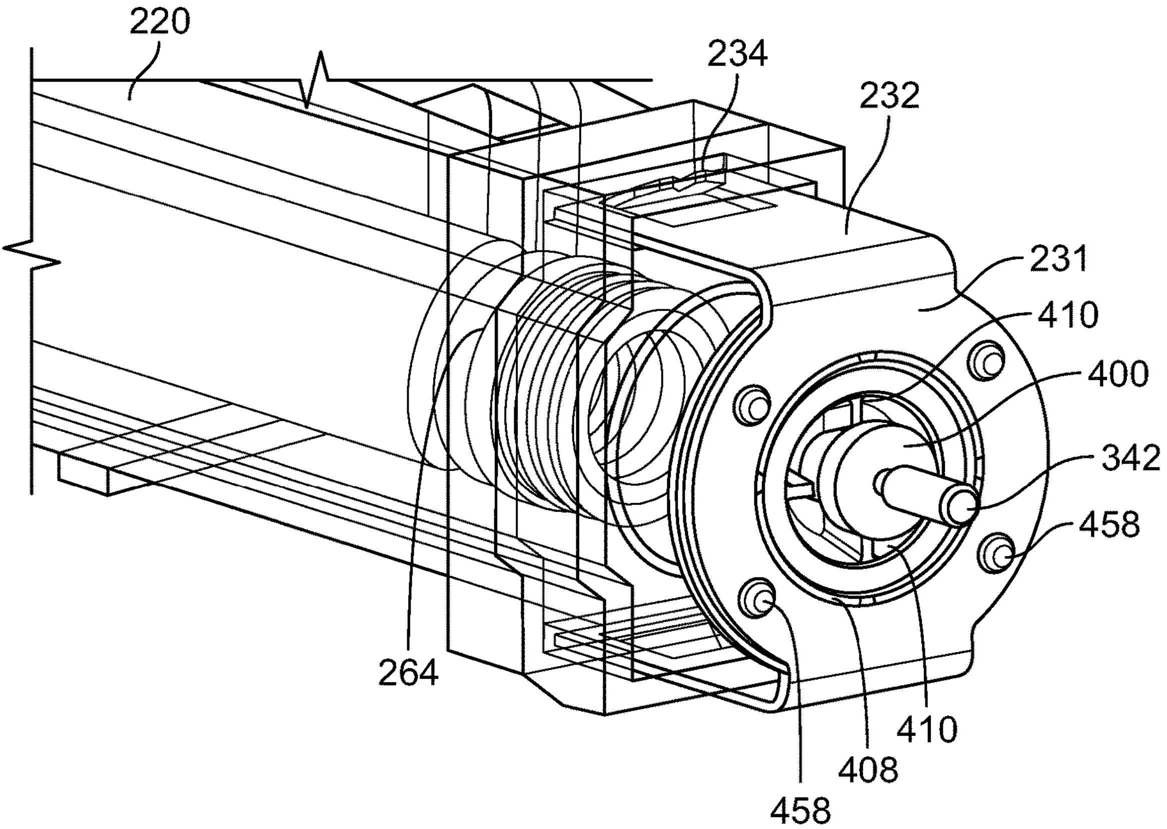
FIG. 17

CASSETTE FOR AN AUTOINJECTOR AND RELATED METHODS

CROSS-REFERENCE TO RELATED APPLICATIONS

This is the United States National Phase of PCT/US20/27576, filed Apr. 10, 2020, which claims priority to U.S. Provisional Patent Application No. 62/835,249, filed Apr. 17, 2019, the entire contents of each of which are hereby expressly incorporated herein by reference.

FIELD OF DISCLOSURE

The present disclosure generally relates to drug delivery devices and, more particularly, to autoinjector devices.

BACKGROUND

Pre-filled hypodermic syringes provide several advantages for the home-use market. These advantages include that pre-filled syringes may be prepared for each medicament with exactly the required dosage. Further, they are easily operated, by merely advancing the plunger-stopper of the syringe. Aside from the costs of the particular medication used, pre-filled syringes are also economically manufactured. Consequently, all these advantages make pre-filled syringes commercially appealing.

Nevertheless, pre-filled syringes also have a significant drawback in the marketplace. Specifically, many users are either frightened by an exposed needle or feel they are inherently incapable of performing an injection. Because of aversions to exposed needles, as well as health and safety issues that may be involved, various types of injectors and other devices have been developed for the specific purpose of concealing needles from the user and automating the injection task to assist the user in performing the injection. One such injector is a reusable autoinjector that receives cartridges having a pre-filled syringe therein. A user orients the autoinjector at a desired injection location, actuates a user input, and a drive or drives of the autoinjector moves the syringe to insert the needle to a subcutaneous location and extrudes a dose of a drug from the syringe with a plunger rod engaging and driving a plunger-stopper through a barrel of the syringe.

Different syringes having varying ranges of barrel diameters can used in the same autoinjector. The plunger-stoppers for such syringes have a similar range of diameters. The size and geometry of the plunger rod used for engaging the variety of plunger-stoppers, however, tends to remain static. A plunger rod suitable for a small diameter barrel and plunger-stopper may provide unsatisfactory operation when used in a larger diameter barrel with a larger plunger-stopper and vice versa.

SUMMARY

In accordance with a first aspect, a cassette for a drug delivery device is disclosed that includes a sleeve, a syringe having a barrel with a distal opening disposed in the sleeve, a plunger-stopper slidably disposed within the barrel, an end cap adapted to couple to the sleeve to secure the syringe in the sleeve, and a spacer sized to be slidably moved within the barrel. The spacer is disposed distal to the plunger-stopper adjacent to the distal opening to be engaged by a plunger rod to slide within the barrel and engage the plunger-stopper.

In some forms, the spacer can have a cup-shaped body with a rearwardly opening cavity sized to receive a plunger rod therein. In further forms, the body can include a plurality of ribs extending inwardly within the cavity.

In some forms, the spacer can include a vent allowing air to flow past the spacer as the spacer is moved along the barrel. In further forms, the vent can include a plurality of passages that extend between radial protrusions arrayed around a circumference of the spacer and/or one or more longitudinal channels that are recessed within an outer surface of the spacer.

In some forms, the end cap can include an interior breakaway portion and the spacer can be secured to the breakaway portion. In further forms, the spacer can be molded over the breakaway portion; the breakaway portion can be a disc and an end wall of the spacer can be molded over the disc. In yet a further form, the breakaway portion can include a side wall portion extending rearwardly from edges of the disc.

In some forms, the cassette can include one or more of the following aspects: the spacer can be sized to frictionally engage an interior surface of the barrel to resist mass forces; the sleeve can include at least one receptacle and the end cap can include an elastomeric bumper adapted to contact a distal end of the syringe and at least one arm member for inserting into the at least one receptacle; the cassette can include a therapeutic product in the syringe.

In some forms, the cassette can further include a housing, where the sleeve is disposed in the housing and movable between first and second positions. In further forms, the cassette can further be provided in combination with an autoinjector.

In accordance with a second aspect, a method for preparing a cassette for an autoinjector is disclosed that includes disposing a plunger-stopper within a barrel of a syringe, disposing the syringe within a sleeve, mounting a spacer sized to be slidably moved in the barrel rearwardly from the plunger-stopper, and coupling an end cap to the sleeve to secure the syringe in the sleeve.

In some forms, mounting the spacer rearwardly from the plunger-stopper can include coupling the spacer to the end cap, such that coupling the end cap to the sleeve aligns the spacer with the barrel. In further forms, coupling the spacer to the end can include molding the spacer over a breakaway portion of the end cap.

In some forms, the method can further include filling the syringe with a therapeutic product and/or receiving a plunger rod of the autoinjector in a rearwardly opening cavity of the spacer for the plunger rod to drive the spacer through the barrel to engage the plunger-stopper.

BRIEF DESCRIPTION OF THE DRAWINGS

FIG. 15 is a perspective view of a first example spacer member of the lock cap of FIG. 13.

FIG. 16 is a perspective view of the spacer member of FIG. 15 and spacer of FIG. 13.

FIG. 17 is a perspective view of a portion of a sleeve, syringe, and lock cap with a fourth example spacer.

DETAILED DESCRIPTION

A cassette for a drug delivery device and related methods are described herein that utilize a spacer to provide an intermediary member between a plunger-stopper of a syringe of the cassette and a plunger rod of the drug delivery device. The spacer can advantageously be provided with a plunger rod reception cavity sized for the plunger rod of the drug delivery device, as well as an end wall sized to engage the plunger-stopper, particularly plunger-stoppers having an annular distal surface. The spacers described herein are sized to be inserted into a barrel of the syringe to engage the plunger-stopper therein and can maintain a radially fixed orientation and resist movement due to mass forces, while producing minimal excess friction. The spacers can further include venting features so that air is not trapped between the spacer and the plunger-stopper when the two objects are moved relative to one another within the barrel. In a drug extrusion operation, the spacer is disposed distal to the plunger-stopper and engaged by a plunger rod to slide within the barrel and engage the plunger-stopper. In some versions, the cassette can include an end cap that couples to the sleeve to secure the syringe therein and the spacer can be coupled to the end cap.

Figure 1:
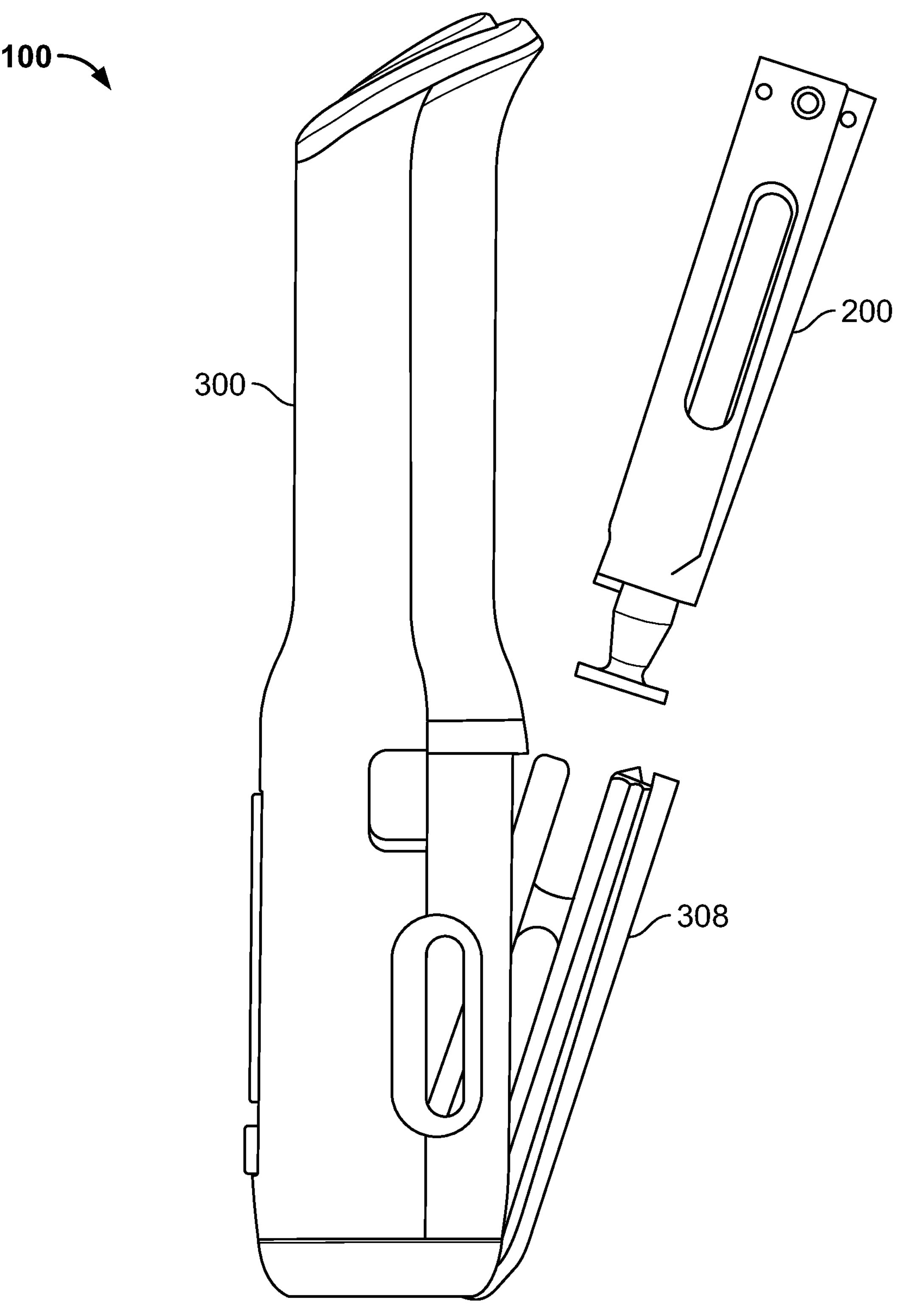
FIG. 1 is an elevational side view of an exemplary embodiment of an autoinjector apparatus including an autoinjector and a cassette.
Figures 23, 24:
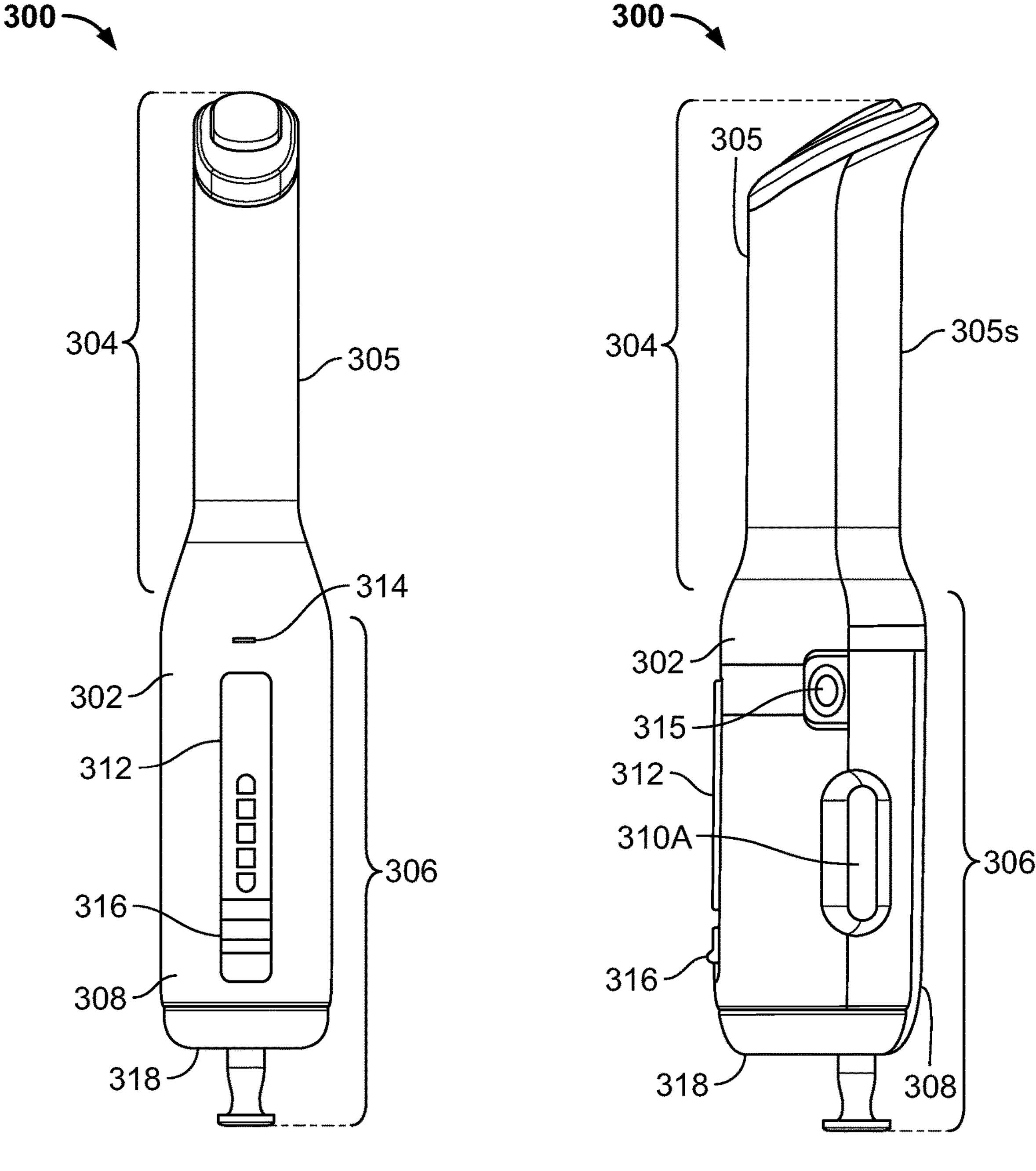
FIG. 23 is a front elevational view of the autoinjector of FIG. 1.
FIG. 24 is an elevational view of the autoinjector FIG. 1.
Figures 25, 26:
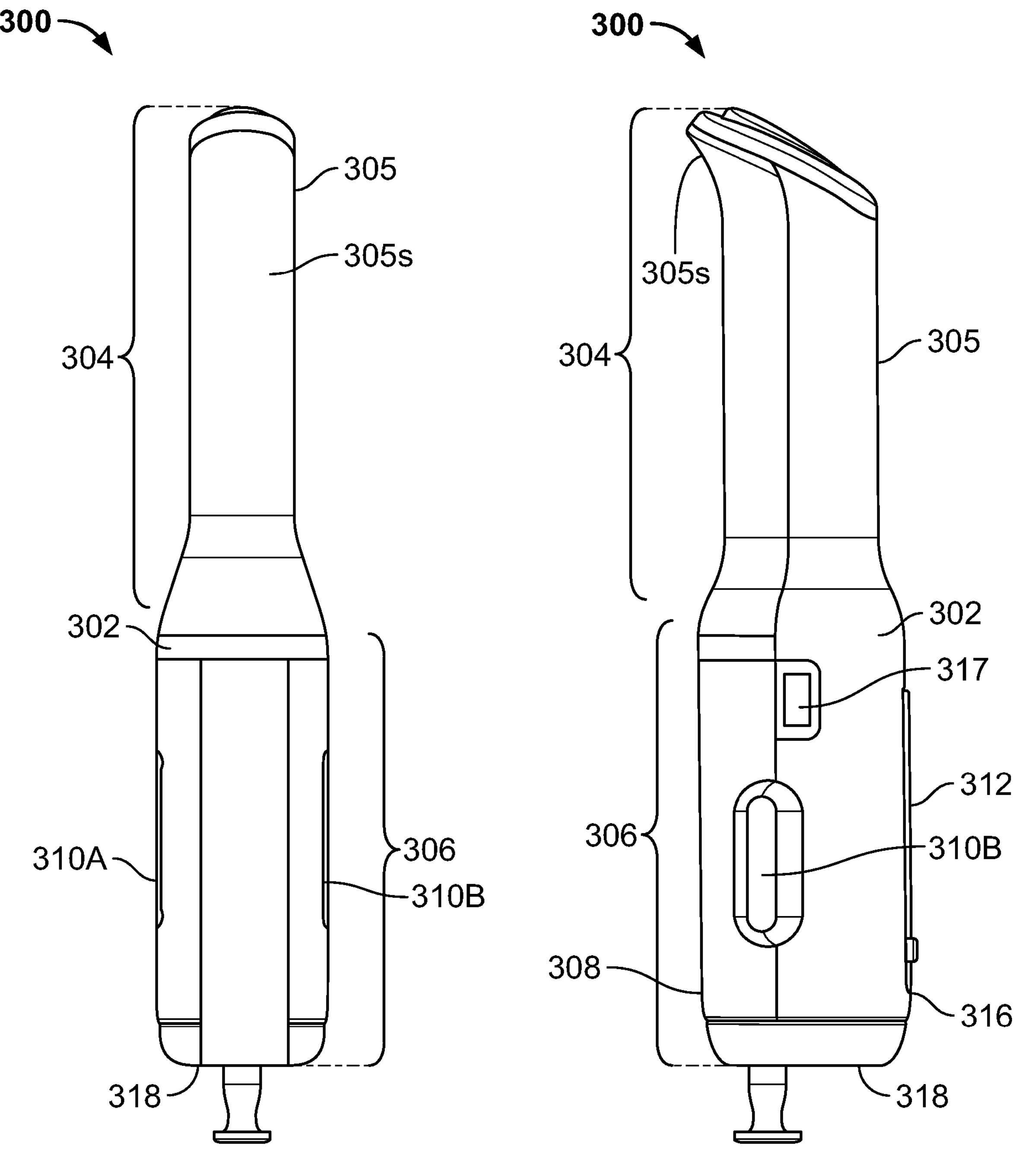
FIG. 25 is a rear elevational view of the autoinjector of FIG. 1.
FIG. 26 is an elevational view of a second side of the autoinjector of FIG. 1.
Figure 27:
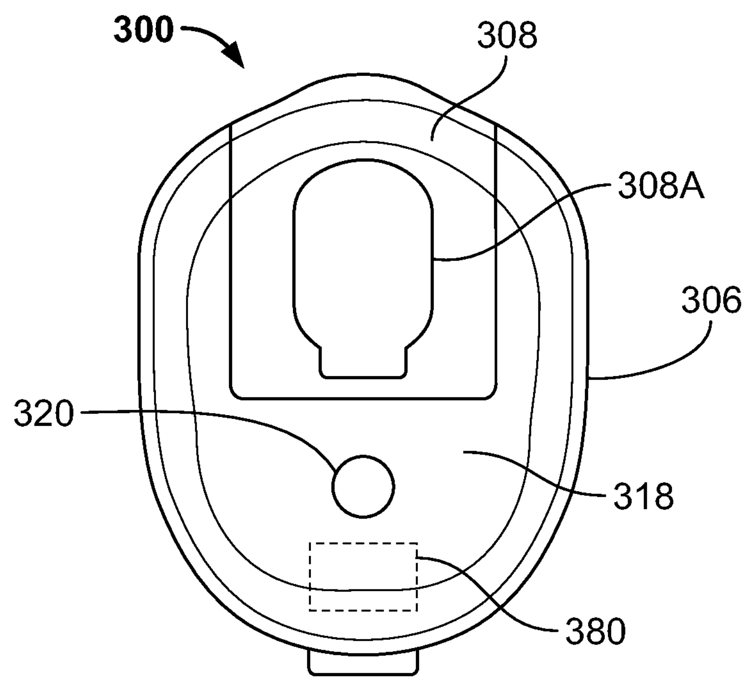
FIG. 27 is an elevational view of a first end of the autoinjector of FIG. 1.
Figure 28:
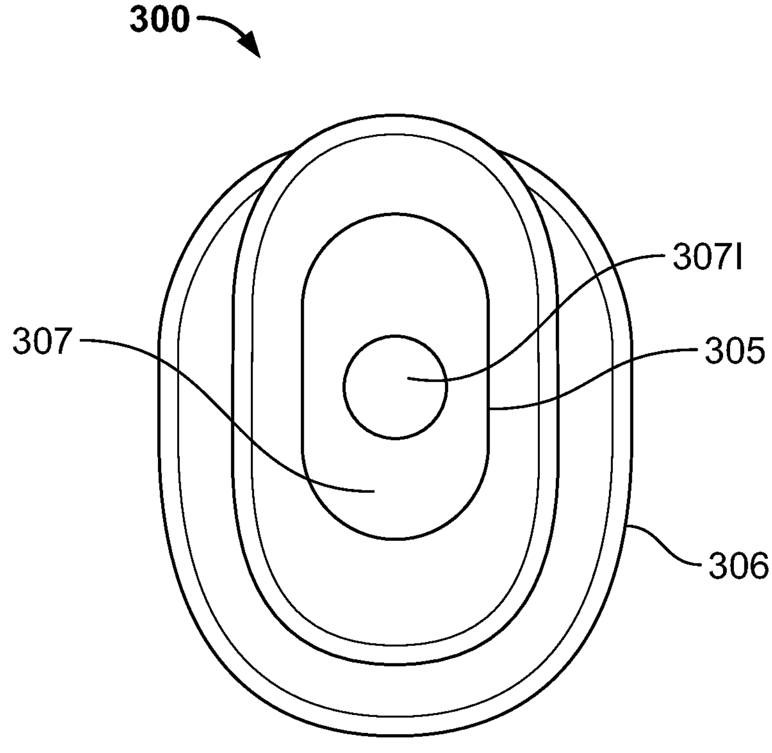
FIG. 28 is an elevational view of a second end of the autoinjector of FIG. 1.

FIG. 1 illustrates an elevational view of an exemplary embodiment of an autoinjector apparatus 100 according to the present disclosure. The autoinjector apparatus 100 comprises an autoinjector 300 and a cassette 200. The autoinjector 300 may comprise a cassette door 308, which in an open position, (as shown) allows insertion therein of the cassette 200, and which in a closed position (e.g., FIG. 24), aligns the cassette 200 with insertion and extrusion drives 330 and 340, respectively (FIG. 29) of the autoinjector 300. The autoinjector 300 may be constructed and adapted for hand-held operation and be reusable. The cassette 200 may be constructed and adapted to house and protect a syringe 260 (e.g., FIG. 2), which may be prefilled with a predetermined dose of a pharmaceutical product. The cassette 200 facilitates and enables easy use of the syringe with the autoinjector 300 and helps prevent needle sticks before and after use. Moreover, the cassette 200 may be constructed and adapted for single, disposable use.

Figure 2:
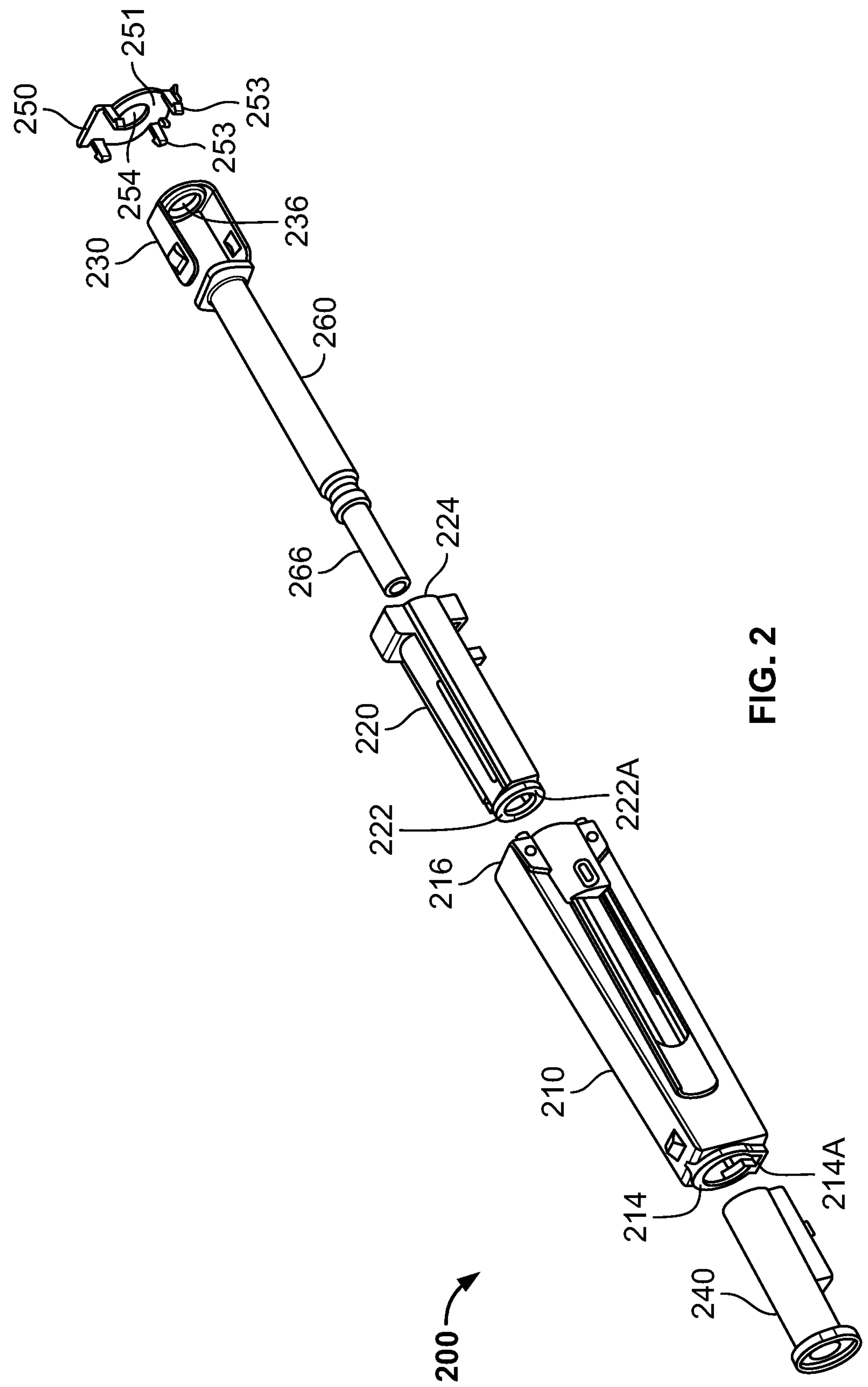
FIG. 2 is an exploded perspective view of an exemplary embodiment of the cassette of FIG. 1 showing an outer housing, an inner sleeve, a syringe, a shield remover, a lock cop, and a cover.

FIG. 2 illustrates an exploded perspective view of an exemplary embodiment of the cassette 200, according to the present disclosure. The cassette 200 may comprise an outer housing 210, an inner sleeve 220 slidably moveable within the outer housing 210, a syringe 260 disposed within or held by the inner sleeve 220, and a shield remover 240 for removing a protective needle shield 266 of the syringe 260. The outer housing 210 may comprise a proximal end wall 214 and an open distal end 216. The proximal end wall 214 of the outer housing 210 may include an aperture 214A having a size and shape for receiving therethrough the shield remover 240. The inner sleeve 220 may comprise a proximal end wall 222 and an open distal end 224. The proximal end wall 222 of the inner sleeve 220 may include an aperture 222A having a size and shape for receiving therethrough the protective needle shield 266 of the syringe 260. The cassette 200 may further comprise an end or lock cap 230 for closing the open distal end 224 of the inner sleeve 220 and securing or locking the syringe 260 within the inner sleeve 220. The cassette 200 may further comprise a cover 250 for closing the open distal end 216 of the outer housing 210. The cover 250 provides for tamper resistance by encasing the inner sleeve 220 and the syringe 260 containing a pharmaceutical product 267, within the outer housing 210 of the cassette 200, and also completes the cosmetic appearance of the cassette 200.

Figure 3:
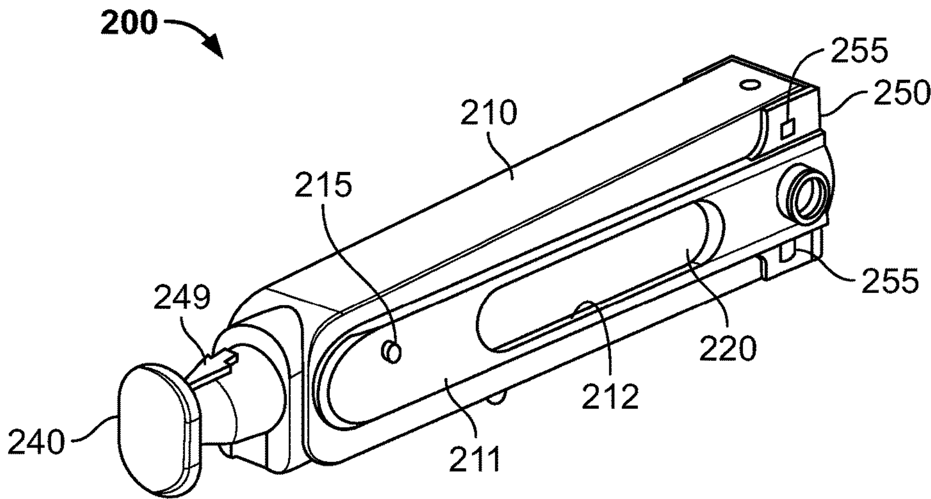
FIG. 3 is a top down front perspective view of the cassette of FIG. 1.
Figure 4:
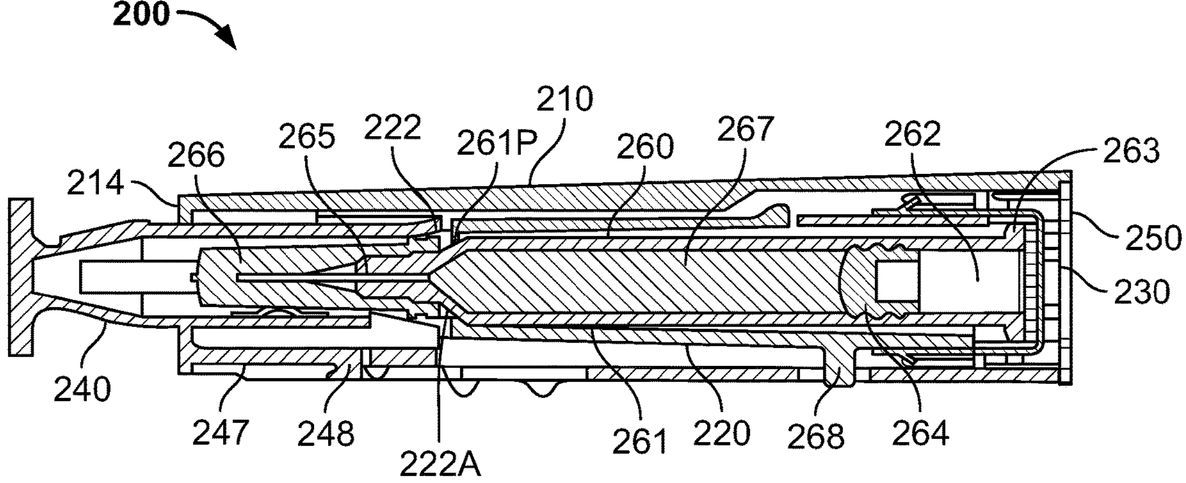
FIG. 4 is a sectional side view of the cassette of FIG. 1.

FIG. 3 illustrates a top down front perspective view of the cassette 200. The outer housing 210 of the cassette 200 may comprise an elongated opening or window 212 in each side wall 211 thereof The windows 212 may be disposed opposite to and aligned with one another. Further, the inner sleeve 220 of the cassette 200 may be made from a transparent, rigid material, such as a clear polycarbonate. The windows 212 in the side walls 211 of the outer housing 210 in combination with the transparent inner sleeve 220, allow viewing of the syringe 260 housed within the inner sleeve 220 (FIG. 4). The wall portions of the inner sleeve 220 viewable through the windows 212 of the outer housing 210 may comprise fill volume indicia (not shown). The outer housing 210 of the cassette 200 may also include a pin 215 or any other suitable mechanical structure that prevents the cassette 200 from being inserted into the cassette door 308 in the wrong direction and/or orientation. An "arrow" icon may be provided on the shield remover 240 or the outer housing 210 (not shown) to indicate the proper direction and orientation of cassette insertion into the cassette door 308.

FIG. 4 illustrates a sectional side view of the cassette 200. As can be seen, the inner sleeve 220 may comprise an inner sleeve pin 268, which may be engaged by an insertion drive 330 of the autoinjector 300 (FIG. 29) during the operation thereof When driven by the insertion drive 330, the pin 268 moves the inner sleeve 220 within the outer housing 210 of the cassette 200. The inner sleeve 220 may be sized and shaped to receive the syringe 260 therein.

Referring still to FIG. 4, the syringe 260 may comprise a barrel 261 that defines a fluid chamber 262. The fluid chamber 262 may be prefilled with a predetermined dose of a pharmaceutical product 267. The pharmaceutical product 267 may have a viscosity that depends on the temperature of the product 267. The syringe 260 may further comprise an injection needle 265 removably or fixedly disposed at a proximal end of the barrel 261, and an outwardly extending flange 263 disposed at a distal end of the barrel 261. The injection needle 265 may communicate with the fluid chamber 262 to allow dispensing of the predetermined dose of a pharmaceutical product 267 expelled from the fluid chamber 262 of the syringe barrel 261. The syringe 260 may further comprise a moveable plunger-stopper 264, disposed within the fluid chamber 262 of the barrel 260, for expelling the predetermined dose of the pharmaceutical product 267 from the chamber 261 so that it may be dispensed through the injection needle 265. The protective needle shield 266 mentioned earlier, covers the injection needle 265 and may be made of a non-rigid material. In one exemplary embodiment, the syringe 260 may comprise a standard 1-mL long glass syringe. The lock cap 230 closes the distal end 224 of the inner sleeve 220 and fixedly secures a proximal end 261P of the syringe barrel 261 against an inner edge surface formed at the junction of the interior surface of the proximal end wall 222 and the aperture 222A of the inner sleeve 220, so that the syringe 260 moves with the inner sleeve 220 as it travels within the outer housing 210, during the operation of the autoinjector 300.

Figures 5, 6:
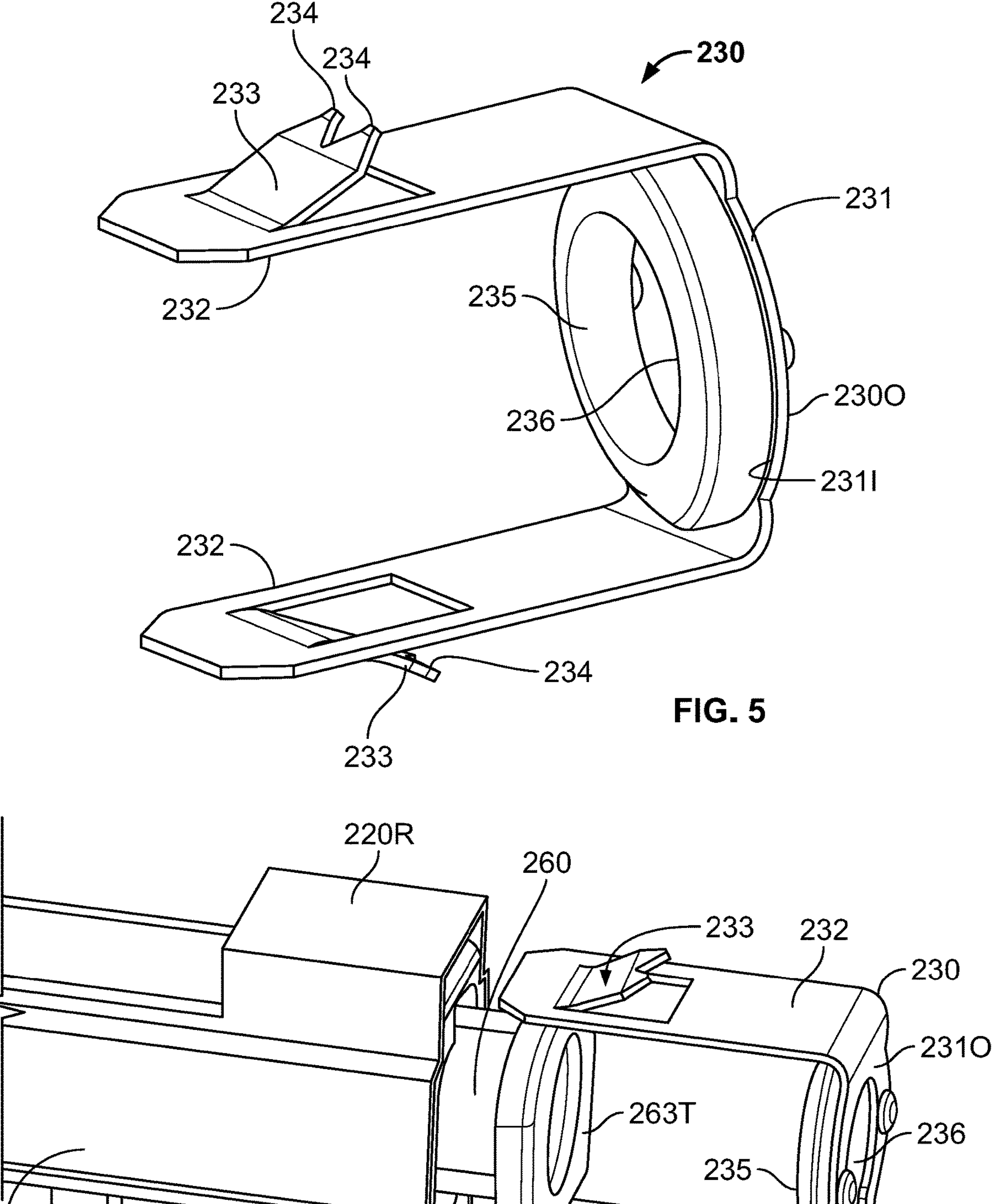
FIG. 5 is a front perspective view of an example lock cap for a sleeve and syringe.
FIG. 6 is a rear perspective view of a portion of a sleeve and a syringe with the lock cap of FIG. 5.
Figure 7:
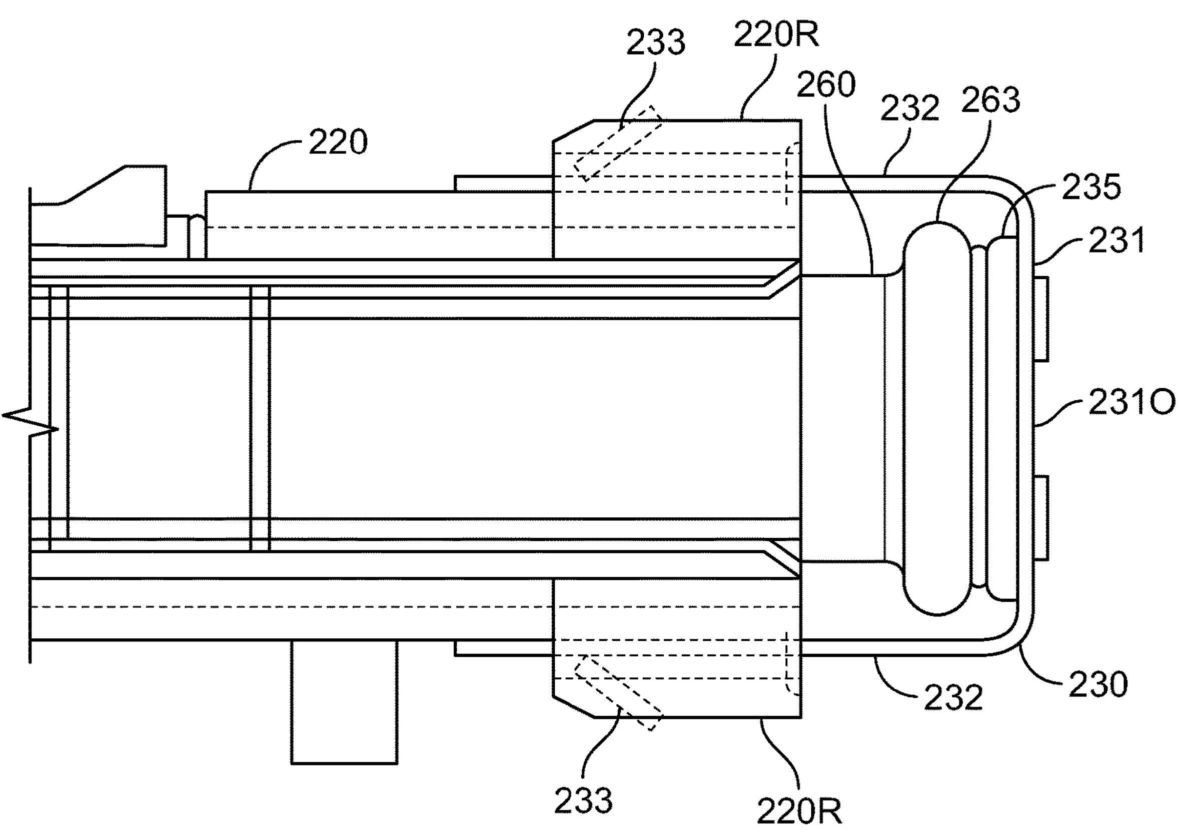
FIG. 7 is a side view of a portion of the sleeve, syringe, and lock cap of FIG. 6.

The lock cap 230, illustrated in FIGS. 5-7, locks the syringe 260 in the inner sleeve 220 with a predetermined force which may be set during assembly of the cassette 200. The lock cap 230 may comprise a generally flat, annular body 231 having outer and inner surfaces 2310 and 2311, and opposing arms 232 depending from the body 231, away from the inner surface 2311 thereof. Each of the arms 232 may comprise a cut-out member 233 with a barbed end 234. In some embodiments, the cut-out members 233 may be spring-like. The members 233 may extend outwardly from the arms 232 and toward the body 231. The body 231 can be made from a metal or rigid plastic material. A soft elastomeric ring-shape bumper 235 may be affixed to the inner surface 2311 of the body 231. The body 231 and bumper 235 may define an opening 236 which can be dimensioned to allow a plunger rod 342 actuated by a motorized extrusion drive 340 of the autoinjector 300 (FIG. 34), to pass through the lock cap 230 and engage and move the plunger-stopper 264 through the fluid chamber 262 of the syringe barrel 261 during the operation of the autoinjector 300. The lock cap 230 may be dimensioned to receive the flange 263 of the syringe 260 between the opposing arms 232 thereof, in a slip-fit manner with the bumper 235 engaging a top surface 263T of the flange 263 as illustrated in FIGS. 6 and 7. The arms 232 of the lock cap 230 may be inserted into opposing receiving receptacles 220R formed at a distal end of the inner sleeve 220 when the syringe 260 is assembled into the inner sleeve 220. The barbs 234 of the arms 232 grip the inner surfaces of the receiving receptacles 220R to lock the lock cap 230 into position, thereby lockingly holding the syringe 260 in the inner sleeve 220. The arms 232 of the lock cap 230 may be inserted into the receptacles 220R of the inner sleeve 220 a selected distance to limit the amount of force (to a predetermined value) applied to the syringe 260 during assembly into the cassette 200 and during usage.

Figure 8:
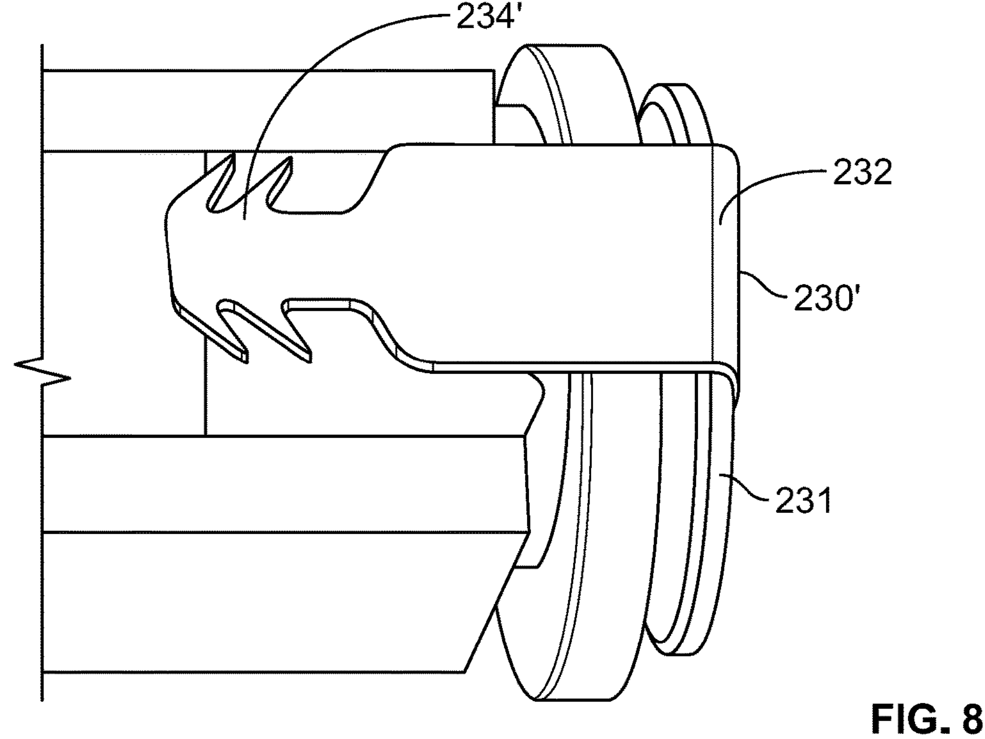
FIG. 8 is a front perspective view of a portion of a sleeve and a second example lock cap.
Figure 9:
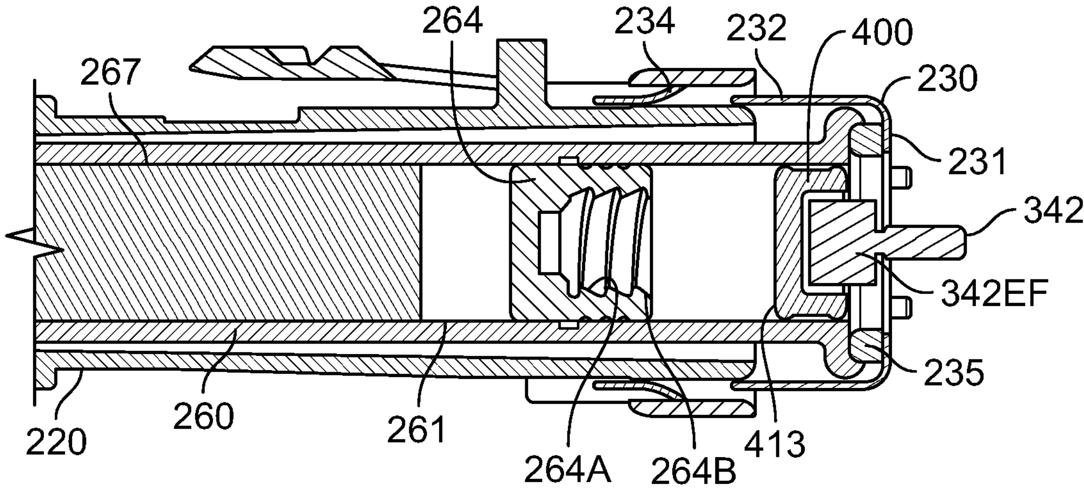
FIG. 9 is a side cross-sectional view of a portion of a sleeve, syringe, and lock cap with a first example spacer.

FIG. 8 illustrates an alternate embodiment of the lock cap numbered 230'. The lock cap 230' is similar to the lock cap 230 of FIGS. 5-7, but omits the cut-out members 233 and instead, provides a barb arrangement 234' at the end of each arm 262.

As shown in FIGS. 9-20, the arrangement of the sleeve 220, lock cap 230, and syringe 260 can include a spacer 400 that is disposed between the plunger rod 342 of the extrusion drive 340 and the plunger-stopper 264 and sized to be moved within the barrel 261. The spacer 400 is located distally or rearwardly of the plunger-stopper 264 and advantageously acts as an adapter so that the size of the barrel 261 and plunger-stopper 264 can be scaled as desired, while the plunger rod 342 can have a reusable single size in the autoinjector 300. As shown in FIGS. 9, 11, 14, and 18, for example, the spacer 400 upon assembly is spaced away from the plunger-stopper 264 by a gap or a space that can be filled simply with ambient air. That is, in some versions the spacer 400 has a diameter that is approximately equal to a diameter of the plunger-stopper 264 and optionally approximately equal to an inner diameter of the barrel 261. As such, the position of the spacer 400 is radially fixed within the barrel 261 during drug delivery when it can move axially within the barrel 261 under an appropriate amount of applied axial force. Thus, as the cassette is assembled the spacer 400 can be selected from a plurality of available spacers, each having different diameters and/or geometries, to have a diameter that matches with the syringe barrel size and plunger-stopper size for any give application.

Figure 12:
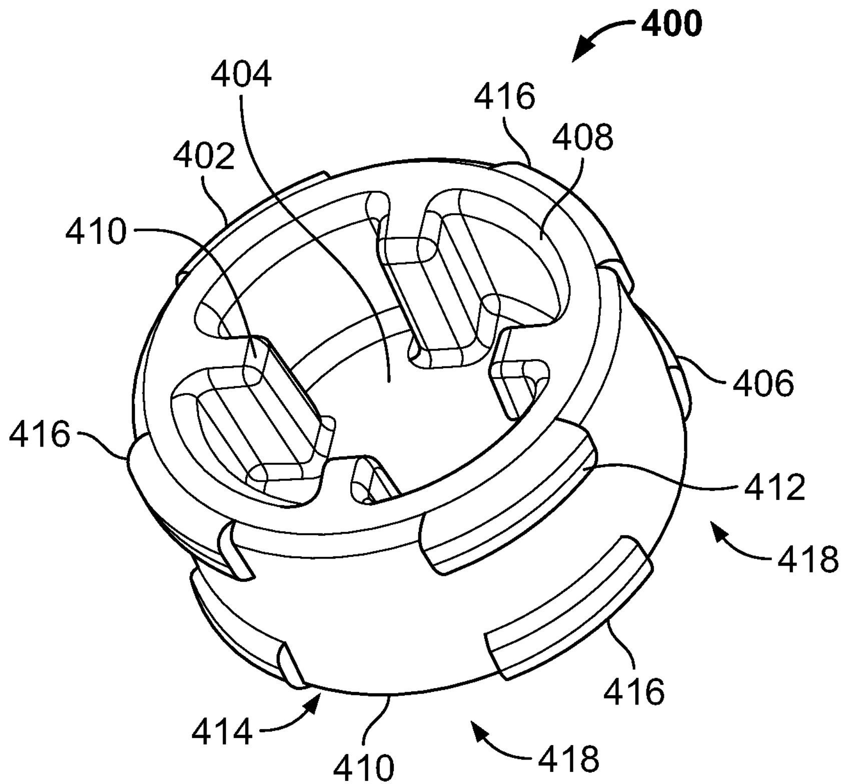
FIG. 12 is a perspective view of the spacer of FIG. 11.
Figure 13:
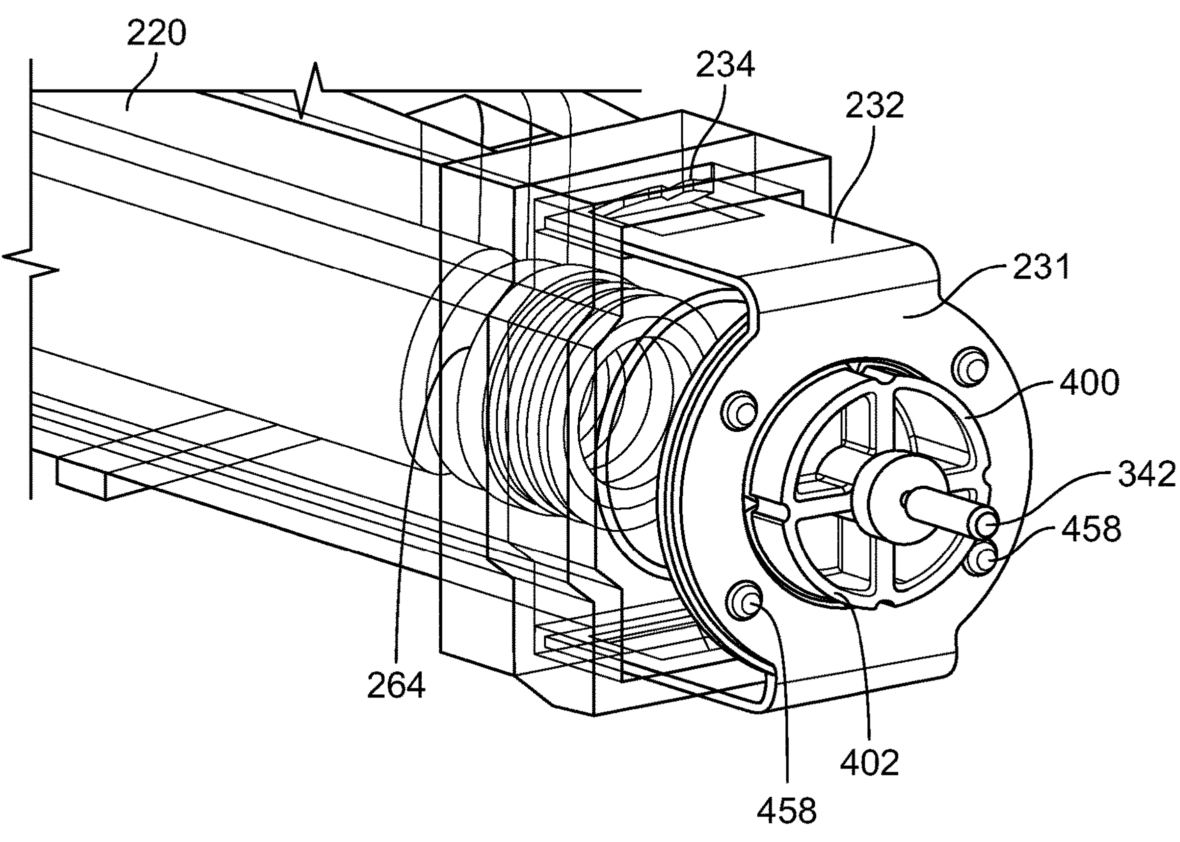
FIG. 13 is a perspective view of a portion of a sleeve, syringe, and lock cap with a third example spacer.
Figure 14:
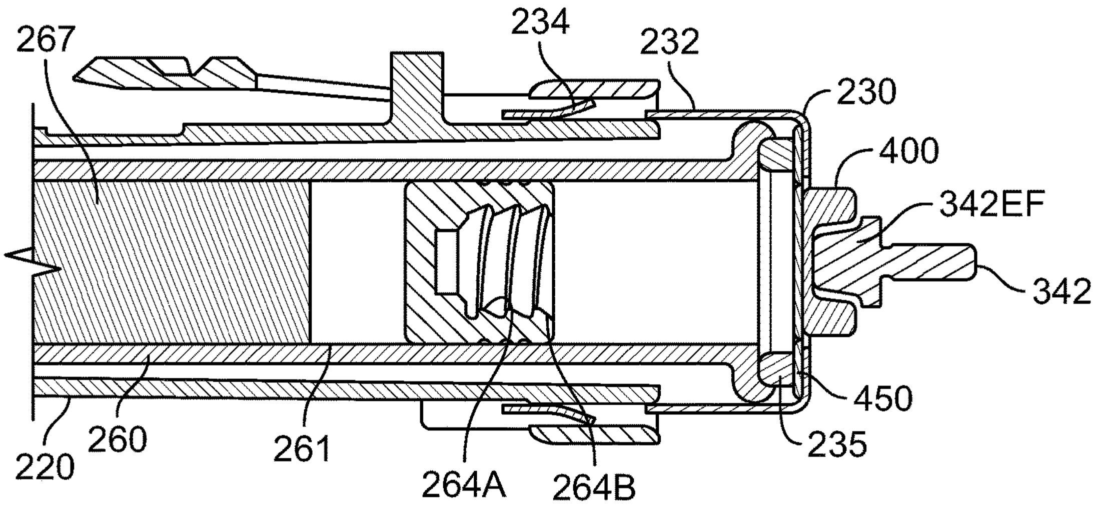
FIG. 14 is a side cross-sectional view of the portion of the sleeve, syringe, lock cap, and spacer of FIG. 13.

The spacer 400 includes a cup-shaped body 402 having a circular end wall 404 and an annular sidewall 406 extending rearwardly from the end wall 404. The body 402 defines a cavity 408 sized to receive an end of the plunger rod 342 therein so that the plunger rod 342 can drive the spacer 400 through the barrel 261. If desired, as shown in the forms of FIGS. 12, 13, and 17, the body 402 can further include a plurality of ribs 410, such as four as shown, that project from the sidewall 406 inwardly into the cavity 408. The ribs 410 can be utilized to engage and/or limit radial movement of the end of the plunger rod 342 while reducing material costs and weight. In some versions, the spacer 400 can be sized so that an outer surface 412 frictionally engages an interior surface of the barrel 261 and resists movement by mass forces, such as gravity and inertia. Preferably, in these forms, the spacer 400 can be sized to resist movement by mass forces, but have minimal or no excess friction beyond that required to resist movement by mass forces. Further, the outer surface 412 preferably orients the spacer 400 and radially fixes the spacer 400 in the barrel 261 by engaging the barrel 261 along a longitudinal length and/or at longitudinally spaced points thereof.

In the illustrated forms, the plunger-stopper 264 can have a cup-shaped configuration defining a rearwardly opening cavity 264A and an annular distal end surface 264B. A front surface 413 of the spacer end wall 404 is sized to engage the distal end surface 264B of the plunger-stopper 264. This advantageously removes issues that arise between the relative sizes of the plunger rod 342 and the plunger-stopper 264, especially the cavity 264A thereof.

Figure 10:
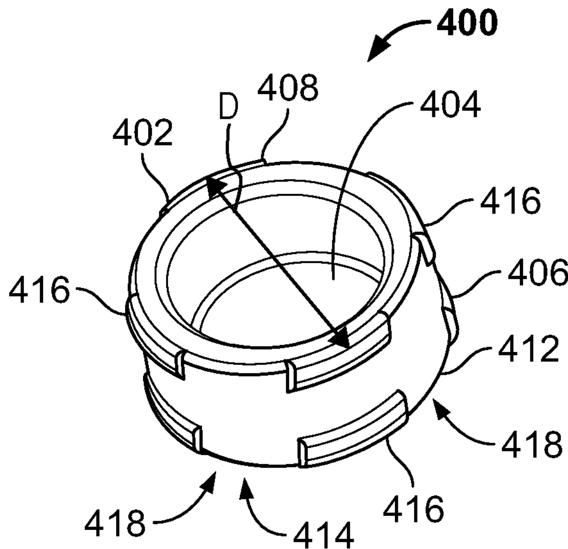
FIG. 10 is a perspective view of the spacer of FIG. 9.
Figure 11:
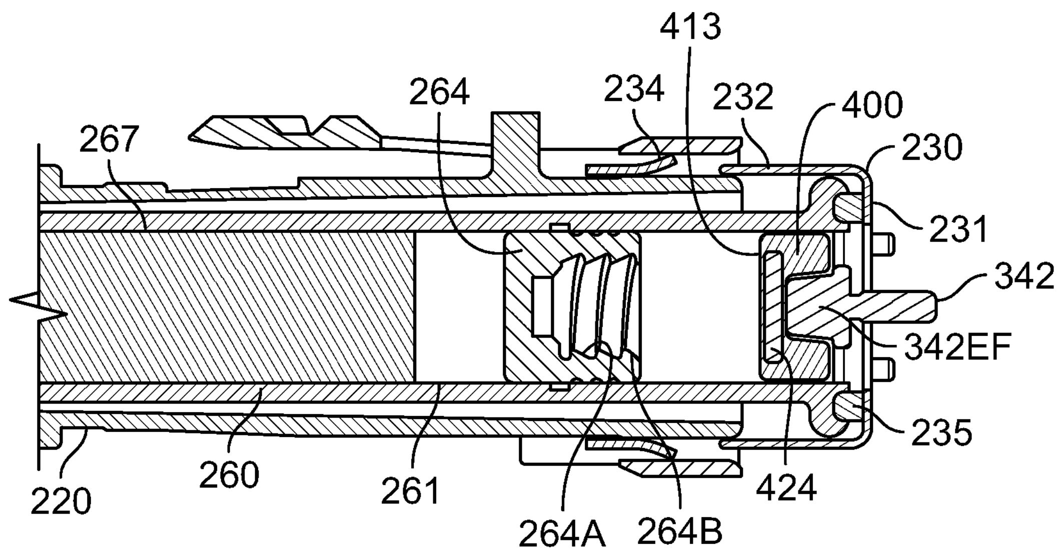
FIG. 11 is a side cross-sectional view of a portion of a sleeve, syringe, and lock cap with a second example spacer.

As shown, the spacer 400 can be remote from the plunger-stopper 264 prior to a drug extrusion operation. In such an arrangement, the spacer 400 must be driven towards the plunger-stopper 264 and the spacer 400 can include one or more vents 414 in or along the outer surface 412 thereof so that air is not trapped between the plunger-stopper 264 and the spacer 400. The vents 412 allow air to flow around the spacer 400 as the spacer 400 is driven through the barrel 261 to engage the plunger-stopper 264. In one form, the spacer body 402 can include protrusions 416 that extend outwardly from the outer surface 412 to engage the interior surface of the barrel 261. In this form, the diameter of the spacer 400 that is approximately equal to a diameter of the plunger-stopper 264 and optionally approximately equal to an inner diameter of the barrel 261 can correspond to an outer diameter of the spacer 400 extending between and including the depth of the protrusions 416 aligned on either side thereof. As a more specific example, FIG. 10 shows a diameter D of the spacer 400 as measured from the respective outer surfaces of the protrusions 416. It will be understood that the other example spacers 400 described herein, such as that shown in FIG. 12, can have a similarly configured diameter D. In the illustrated forms, the protrusions 416 are arrayed in a ring around a circumference of the body 402 and are spaced from one another, such that passages 418 between protrusions 416 act as the vents 412. In order to orient the spacer 400 within the barrel 261, the body 402 can include two rings of protrusions 416, which can be disposed adjacent to the end wall 404 and a distal end 420 of the sidewall 406, as shown. The longitudinal thickness of the protrusions 416 can be modified to control the amount of friction generated between the spacer body 402 and the barrel 261. In an additional or alternative form as shown in FIG. 16, the spacer body 402 can include one or more longitudinal channels 422 recessed in the outer surface 412 to act as the vents 412. The channels 422 can extend along the outer surface 412 between adjacent ones of the protrusions 416, for example, to provide additional venting for the spacer 400.

In some embodiments, shown in FIGS. 9-12, the spacer 400 can be disposed within the barrel 261 in a storage position prior to a drug extrusion operation. The storage position of the spacer 400 in these embodiments is distal of the plunger-stopper 264, but within the barrel 261. The spacer 400 can be spaced from the plunger-stopper 264 as shown or can be inserted into the barrel 261 until the end wall 404 engages the distal end surface 264B of the plunger-stopper 264. In a first embodiment of FIGS. 9 and 10, the spacer 400 includes two rings of four protrusions 416 each and no ribs 410 within the cavity 408. This embodiment may be particularly suitable for barrels 261 having a relatively smaller diameter, such that the cavity 408 is sized to receive an end 342 of the plunger rod 342 therein with minimal, e.g., between about 1 mm to about 5 mm or between about 1 mm to 3 mm, spacing therearound. In a second embodiment of FIGS. 11 and 12, the spacer includes two rings of four protrusions 416 each and four ribs 410 within the cavity 408 to reduce a cross-sectional area for reception of the plunger rod end 342EF. This embodiment may be particularly suitable for barrels 261 having a relatively larger diameter, such that the cavity 408 has a much larger, e.g., greater than 5 mm, diameter than the plunger rod end 342EF. In some examples, the smaller diameter barrels can have an inner diameter of up to about 7 mm, or about 6.35 mm, and the larger diameter barrels can have an inner diameter of greater than 7 mm, or about 8.65. With regard to drug dosages, the smaller diameter barrel can have a volume to receive 1 mL of a drug and the larger diameter barrel can have a volume to receive 2.25 mL of a drug. If desired, particularly for larger diameter spacers 400, the spacer 400 can include a rigid insert 424 disposed or embedded within the end wall 404 to provide additional rigidity to the end wall 404 to minimize undesirable deformation during a drug extrusion operation. The insert 424 can preferably be spaced from the front surface 413 and edges of the end wall 404. In the illustrated example, the insert 424 can be a disc of plastic, metal, or other sufficiently rigid material.

In other embodiments, shown in FIGS. 13-20, the spacer 400 can be coupled to the end cap 230, such that securing the end cap 230 to the sleeve 220 aligns the spacer 400 with the barrel 261. Specifically, the end cap 230 can include a spacer member 450 that is secured to the annular body 231. As shown, the spacer member 450 has a body 452 with an annular outer portion 454 sized to fit between the arms 232 of the end cap 230, such that the annular outer portion 454 can be mounted between the bumper 235 and the annular body 231. Pursuant to this, the annular outer portion 454 can include a plurality of openings 456 extending therethrough to receive fasteners 458 securing the bumper 235 and spacer member 450 to the annular body 231. As shown, the spacer member body 452 further includes an interior breakaway portion 460. The breakaway portion 460 is spaced radially inwardly from the outer portion 458 and attached thereto a plurality of bridges 462, such as four as shown, that are configured to break when a force is applied in a direction generally normal to the main surface of the spacer member 450.

In a first form shown in FIGS. 13-16, the breakaway portion 460 has a disc-shaped, planar body 464 and the end wall 404 of the spacer 400 is secured to the breakaway portion 460 so that the sidewall 406 extends rearwardly away from the end cap 230. In the illustrated form, the front surface 413 of the end wall 404 can be secured to the disc-shaped body 464 by any suitable method, including adhesive, ultrasonic welding, and so forth, so that the entire spacer body 402 is rearward of the spacer member 450 and disposed entirely outside of the barrel 261 in a storage position prior to a drug extrusion operation. In another form, the end wall 404 can be molded over the breakaway portion 460. The breakaway portion 461 can include openings therein to receive material of the spacer 400 therein during the molding process and aid in securing the components together.

Figure 18:
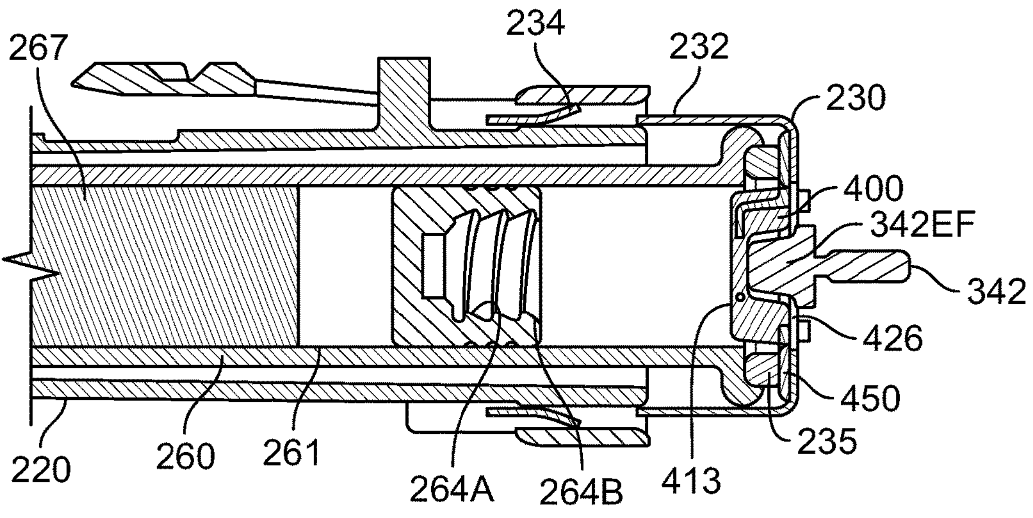
FIG. 18 is a side cross-sectional view of the portion of the sleeve, syringe, lock cap, and spacer of FIG. 17.
Figure 19:
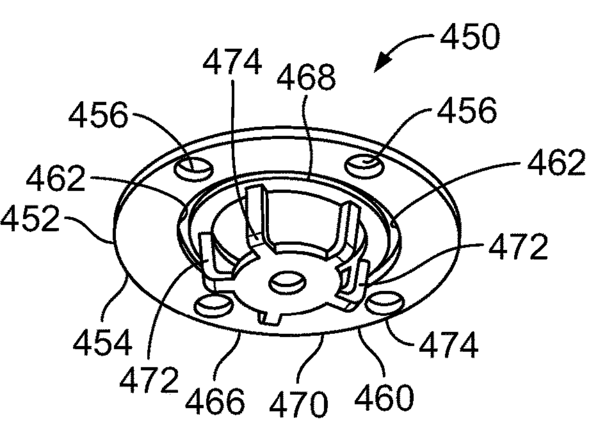
FIG. 19 is a perspective view of a second example spacer member of the lock cap of FIG. 17.
Figure 20:
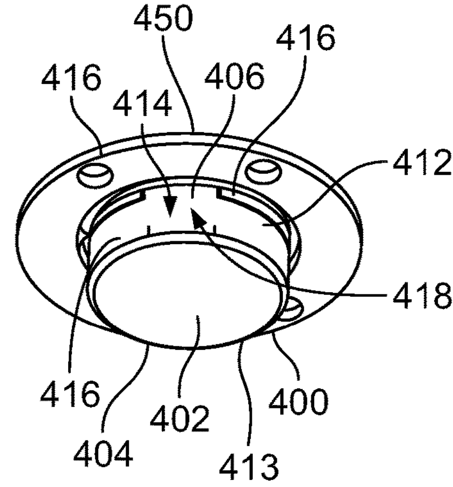
FIG. 20 is a perspective view of the spacer member of FIG. 19 and spacer of FIG. 17.

In a second form shown in FIG. 17-20, the breakaway portion 460 has a basket-shaped body 466 with an annular top wall 468, a disc-shaped or annular bottom wall 470, and a side wall portion having plurality of ribs 472, e.g., three, four, five, six, or more, extending between the top and bottom walls 468, 470. The bottom wall 470 is spaced longitudinally from the top wall 468 and has a diameter sized smaller than the interior diameter of the annular top wall 468. In the illustrated form, the ribs 472 each have an elbow portion 474 such that the ribs 472 extend downwardly from the top wall 468 until the elbow portion 474 which turns the ribs 472 radially inwardly to connect to the bottom wall 470. With this form, the spacer body 402 can be molded over the basket-shaped body 466 with the top wall 468 adjacent to or coplanar with a distal surface 426 of the spacer sidewall 406, the bottom wall 470 embedded within the end wall 404, and the ribs 472 embedded within the sidewall 406 and, if applicable, the end wall 404. As shown, the spacer distal surface 426 can abut the annular body 231 of the end cap 230. With this form, due to the basket-shaped body 466 extending forwardly from the end cap annular body 231, when the end cap 230 is secured to the sleeve 220, the spacer 400 can partially project into the interior of the barrel 261, as shown in FIG. 18.

It will be understood that any of the spacers 400 described herein can be utilized with the housing 210 to form a portion of the cassette 200. Further, the cassette 200, having the spacer 400 therein, can be inserted into the autoinjector 300 as described herein. As such, during a drug extrusion operation, the plunger rod 342 can be driven longitudinally through the autoinjector 300 to engage the spacer 400 and drive the spacer 400 through the barrel 261 to engage the plunger-stopper 264 and thereafter drive the spacer 400 and the plunger-stopper 264 through the barrel 261 to extrude a dose of a drug from the syringe 260. The two or all of the components can be in contact with one another in a storage position prior to a drug extrusion operation or can be spaced from one another and brought into contact by movement of the plunger rod 342.

Figure 21:
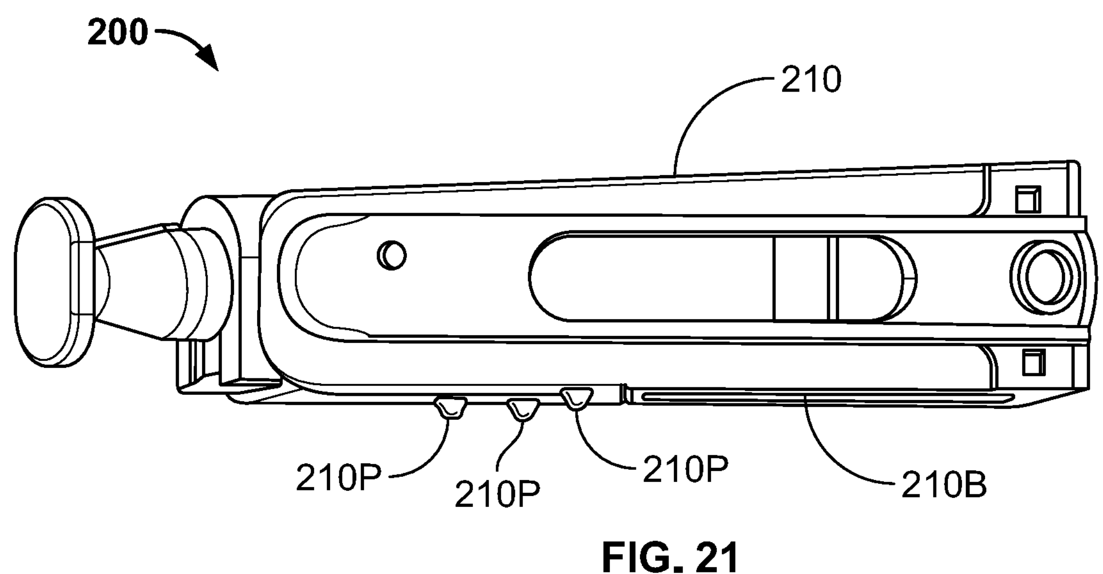
FIG. 21 is a bottom up, front perspective view of the cassette of FIG. 1 showing a bottom surface with projections.
Figure 22:
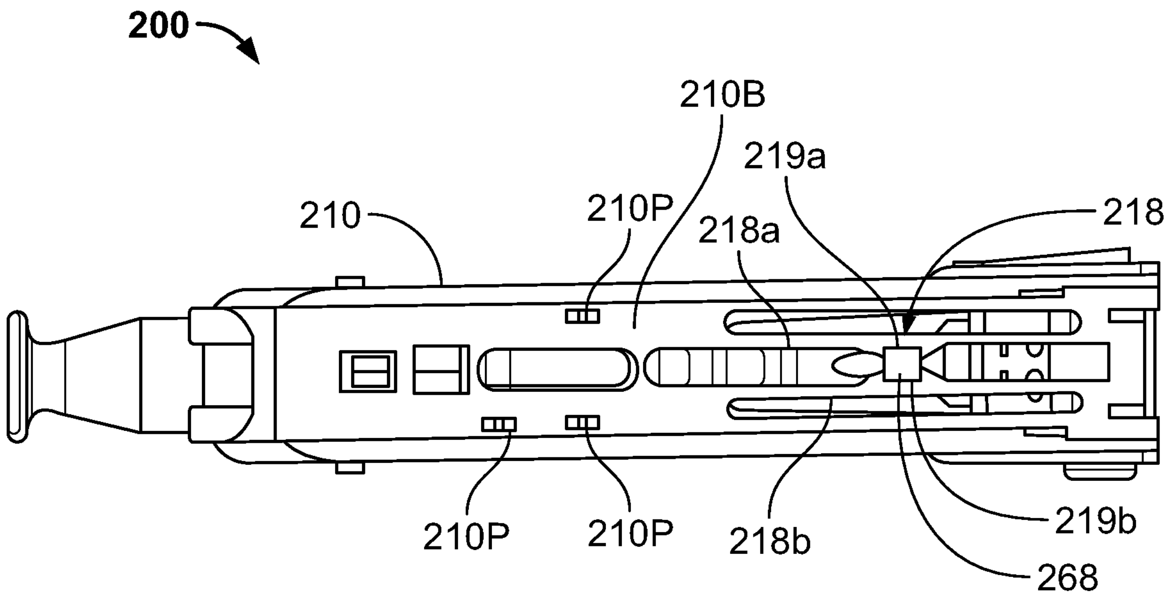
FIG. 22 is a bottom view of the cassette of FIG. 21 showing the projections and a latch mechanism.

Referring to FIGS. 21 and 22, the outer housing 210 of the cassette 200 may comprise a cassette identification arrangement which provides information that identifies the cassette 200, e.g., information about the contents of the syringe 260 contained within the cassette 200 and/or other cassette/syringe characteristics. In one exemplary embodiment, the cassette identification arrangement may comprise one or more bumps or projections 210P provided on a bottom surface 210B of the outer housing 210 of the cassette 200. The projection(s) 210P may be sensed by or engage a detector (not shown) in the autoinjector 300 when the cassette 200 is inserted into the door 308 of the autoinjector 300 and the door 308 is closed. The detector 370 may be electrically coupled to a microprocessor (e.g. microprocessor 350 illustrated in FIG. 29) contained within the autoinjector 300, which enables the autoinjector 300 to read the cassette identification arrangement to thereby identify the cassette 200. In one exemplary embodiment, a predetermined number of projections 210P may be located on the bottom surface 210B of the outer housing 210 in predetermined locations, and the detector 370 may comprise a key pad of plural keys (not shown). Certain ones of the plural keys may be actuated by the cassette projections 210P when the cassette 200 is installed in the autoinjector 300, depending upon the location and number of the projections 210P. Each key actuated by one of the projections 210P may provide information that allows the autoinjector 300 to identify the cassette 200. In some embodiments, the cassette identification arrangement identifies the drug delivery profile of the pharmaceutical product provided in the cassette 200. Therefore, upon insertion and recognition of a valid cassette and the information provided by cassette identification arrangement, available preset drug extrusion speed ranges commensurate with the drug delivery profile of the pharmaceutical product provided in the cassette 200 may be automatically registered by the autoinjector 300. Available speed ranges are dependent upon the syringe fill volume and pharmaceutical product characteristics, such as viscosity. For example, but not limitation, if the cassette identification arrangement comprises plural projections 210P, one projection may indicate a 1 mL fill and two projections may indicate a 0.5 mL fill and additional projections may be provided to identify the pharmaceutical product and/or characteristics.

FIG. 22 also illustrates a latch mechanism 218 that may be provided on the bottom wall 210B of the outer housing 210 of the cassette 200. The latch mechanism 218 may include a pair of parallel extending, resilient locking arms 218*a*, 218*b*. The locking arms 218*a* and 218*b* may each define a locking detent slot 219*a* and 219*b*, respectively. The pin 268 of the inner sleeve 220 may engage the detent slots 219*a*, 219*b* of the latch mechanism 218 when the syringe 260 is in a home position with the injection needle 265 of the syringe 260 concealed in the cassette 260 in a needle concealed position, thereby locking of latching the inner sleeve 220 into place within the outer housing 210 of the cassette 200. During an injection cycle, the insertion drive 330 of the autoinjector 300 (FIG. 29) may spread the resilient locking arms 218*a*, 218*b* apart to unlatch or release the inner sleeve pin 268 from the detent slots 219*a*, 219*b* of the latch mechanism 218, thereby allowing the unlatched inner sleeve 220 containing the syringe 260 to be freely moved by the insertion drive 330, which pushes on the inner sleeve pin 268 to move the inner sleeve 220 relative to the outer housing 210 from the home position, where the injection needle 265 is in the needle concealed position, to an injection position, where the injection needle 265 is in a needle extended position that allows it to penetrate the skin at the injection site. At the end of the injection, cycle, the insertion drive 330 pulls the inner sleeve pin 268 back into the detent slots 219*a*, 219*b*, thereby returning the inner sleeve 220 (which contains the syringe 260) to the home position, where the injection needle 265 is in the needle concealed position.

Cassettes of similar structure and operation are described in greater detail in the following patent applications, each of which is incorporated herein by reference in its entirety: US Publ. Nos. 2009/0292246 and 20100022955; and PCT Publ. No. WO 2009/143255.

Referring again to FIGS. 2-4, the cover 250 attaches to a distal end of the outer housing 210 of the cassette 200 to close a distal end of the cassette 200. The cover 250 may be a generally planar member having a shape which matches that of the distal end 216 of the outer housing 210. The cover 250 may comprise two or more locking arms 253 that extend from an inner surface 251 of the cover 250 and lockingly engage corresponding receptacles 255 extending through the side walls 211 of the outer housing 210. In addition, any detent structure or other suitable locking arrangement (not shown) formed in, on, or through the outer housing 210, adjacent to the distal end 216 thereof may be used for attaching the cover 250. The cover 250 may further comprise an opening 254 which axially aligns with the opening 236 defined by the lock cap 230. The opening 254 in the cover 250, like the opening 236 of the lock cap 230, may be dimensioned to allow the plunger rod 342 actuated by the motorized extrusion drive 340 of the autoinjector 300 (FIG. 29), to pass through the cover 250 and engage and move the plunger-stopper 264 through the fluid chamber 262 of the syringe barrel 261 during the operation of the autoinjector 300.

Referring now to FIGS. 23-28, the autoinjector 300 may comprise a casing 302 having a handle section 304 and a cassette receiving section 306 inline with the handle section 304. To aid patients with manual dexterity issues, the handle section 304 of the autoinjector casing 302 may define an ergonomically shaped handle 305 with a soft grip area 305S. The cassette receiving section 306 comprises the cassette door 308 (FIGS. 24 and 26) described earlier. The cassette door receives the cassette 200 in an open position (FIG. 1) and aligns the cassette 200 with insertion and extrusion drives, and other structures and components of the autoinjector 300 in a closed position. The cassette door 308 may include a "cassette" icon that indicates the insertion entry point for the cassette 200. The cassette receiving section 306 of the casing 302 may comprise windows 310A, 310B on opposing sides thereof that align with the windows 212 (FIG. 3) of the cassette 200 when the cassette door 308 is closed with the cassette 200 correctly installed therein. In one or more embodiments, the windows 310A, 310B may be double-layered. One or more lights (not shown) may be provided inside the casing 302 to evenly backlight illuminate the cassette windows 212 and the syringe 260 disposed within the inner sleeve 220 of the cassette 200, so that the user can observe the injection cycle through the windows 310A, 310B of the autoinjector 300, i.e., observe the initial and end positions of the plunger-stopper 264 of the syringe 260 during the syringe content (hereinafter "drug") extrusion process, as well as syringe movements within the cassette 200.

Referring still to FIGS. 23, 24, 26, and 28, the autoinjector 300 may further comprise a user interface 312 and an audio speaker (not shown). The user interface 312 (best illustrated in FIG. 23) may be located in the cassette receiving section 306 of the casing 302, and provides various visual indicators. The audio speaker may be disposed inside the casing 302 and provides various audible indicators. The audio speaker may audibly communicate with the external environment via a speaker aperture 314 formed in the casing 302 in the cassette receiving section 306. The visual and audible indicators generated by the user interface 312 and the audio speaker can tell the user when the autoinjector 300 is ready for use, the progress of the injection process, injection completion, the occurrence of any errors, and other information. The autoinjector 300 may further comprise one or more of a settings/mute switch 315, a speed selector switch 316, a start button 307, and an eject button 317. The settings/mute switch 315 (FIG. 24) may be located in the cassette receiving section 306 of the casing 302. The mute switch 315 may be constructed and adapted allow the user to turn on and off all synthesized sounds, except error sounds, and to respond in real-time so that if the user begins the injection process and changes the mute switch to off, the sounds are immediately muted. The mute switch 315 may also be constructed and adapted to slide toward a "mute" icon to mute the audio speaker. A light indicator may be provided to confirm the "mute" state. The speed selector switch 316 (FIGS. 23 and 24) may be located in the cassette receiving section 306 of the casing 302. The speed selector switch 316 may be constructed and adapted to allow the user to select among a plurality of preset drug delivery (extrusion) speeds to accommodate personal patient preference. The speed selector switch 316 may comprise a three switch positions. Other embodiments of the speed selector switch may comprise two switch positions, or 4 or more switch positions. In still other embodiments, the speed selector switch may be of the infinitely variable type. In some embodiments, changing the position of the switch 316 prior to injection changes the speed of drug extrusion during injection while changing the position of the speed selector switch 316 during injection, does not change the speed of the injection in real time. The autoinjector 300 may also be provided with one or more demo cassettes to allow the user to experiment with different speeds of drug delivery. The start button 307 at a free end of the handle 305. The button 307 may include an indentation 3071 for optimizing thumb placement on the button 307. The button 307 may be made of a translucent material that allows a lighting effect to illuminate the button as signals. The eject button 317 (FIG. 26) may be located in the cassette receiving section 306 of the casing 302. The eject button 317 may include an indentation 3171 for optimizing finger placement on the button 317. In some embodiments, the eject button 317 may be controlled by the microprocessor (e.g. microprocessor 350 illustrated in FIG. 29) of the autoinjector 300, which may be programmed to eliminate accidental inputs during the injection process.

Referring again to FIG. 27, the cassette receiving section 306 of the casing 302 and the cassette door 308 may form a proximal end wall 318 of the autoinjector 300. The proximal end wall 318 may be configured as a broad, flat and stable base for easily positioning the autoinjector 300 on a support surface, after removal of the shield remover 240 or when the autoinjector 300 does not contain the cassette 240. The portion of the proximal end wall 318 formed by the cassette door 308 may include an aperture 308A that is sized and shaped to allow the shield remover 240 to be removed from the cassette 200 and withdrawn through the aperture 308A, when the cassette 200 is installed in the autoinjector 300. As soon as the shield remover 240 passes out through the aperture 308A, the tongues 245T of the expandable partial collar structure 245 expand or spread outwardly, thereby preventing the shield remover 240 and the needle shield 266 attached thereto from being re-inserted into the aperture 308A of the cassette door 308. The proximal end wall of the autoinjector 300 may further comprise a target light 320. The target light 320 may be constructed and adapted to turn on when the shield remover 240 is removed from the cassette 200 and withdrawn through the aperture 308A, thereby visually indicating that the shield remover 240 has been removed. Once turned on, the target light aids the user in visualizing and selecting an injection site.

Figure 29:
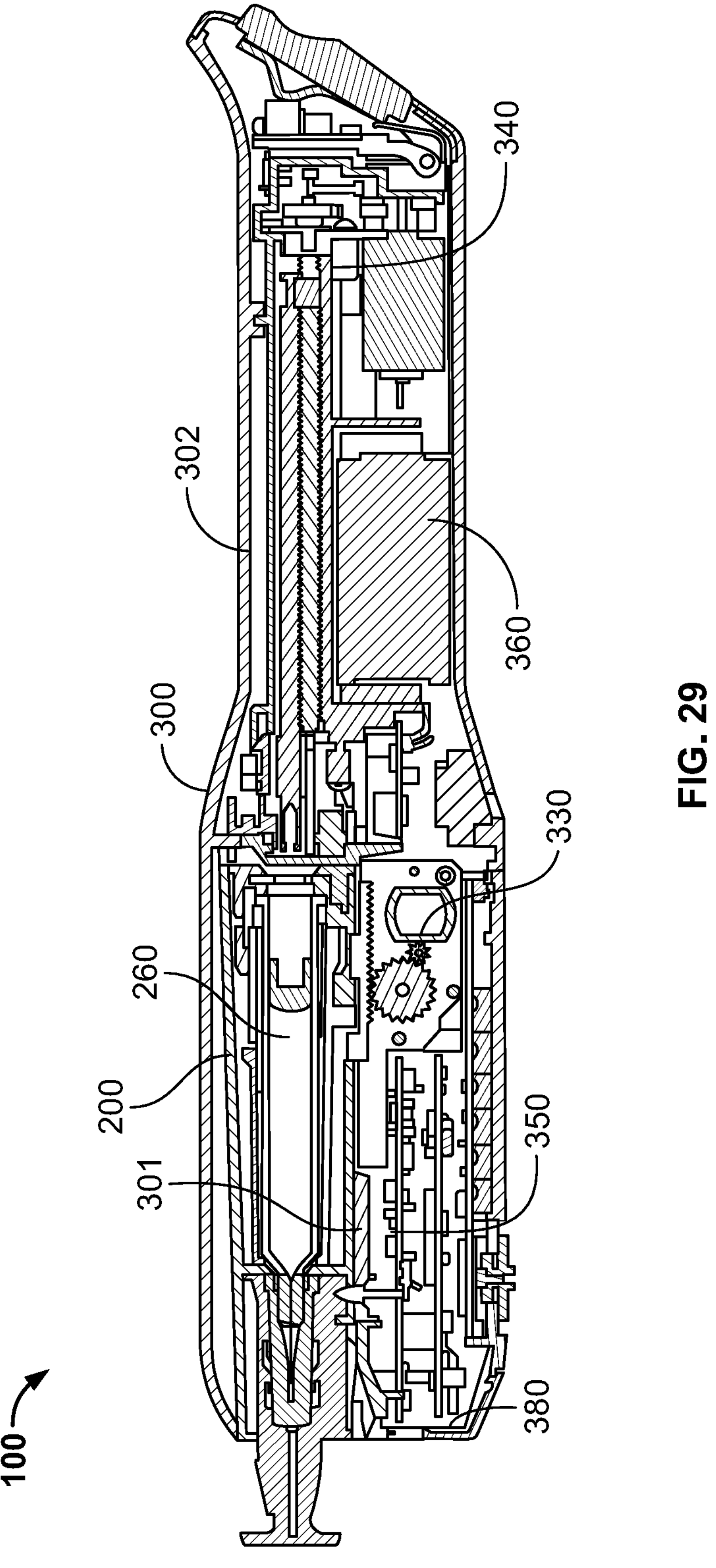
FIG. 29 is a sectional side view of the autoinjector and cassette of FIG. 1.

FIG. 29 illustrates a sectional side view of the autoinjector apparatus 100. comprising the autoinjector 300 and the cassette 200 installed therein. The casing 302 of the autoinjector 300 may house a chassis 301 for receiving the cassette 200 that contains the syringe 260, a motorized insertion drive 330, a motorized extrusion drive 340, a microprocessor 350 (described earlier), a battery 360 for powering the drives 330, 340 and the microprocessor 350, and the skin sensor 380 (described earlier).

The microprocessor 350 may be programmed with certain instructions that executed by the microprocessor 350 enable it to control and monitor the various operations and functions of the autoinjector 300. For example, but not limitation, the microprocessor may be programmed with instructions for controlling the motorized insertion and extrusion drives 330, 340 such that it controls and monitors each step of the injection cycle and process flow, thereby automating needle insertion, drug extrusion, and needle retraction and ensuring accurate, consistent, and reliable operation of the autoinjector 300 and pharmaceutical product administration. The microprocessor may also be programmed with instructions for controlling the audible and visual feedbacks to the user. An automated power-on self-test checks the operation of the autoinjector 300 and remaining battery charge.

Figure 30:
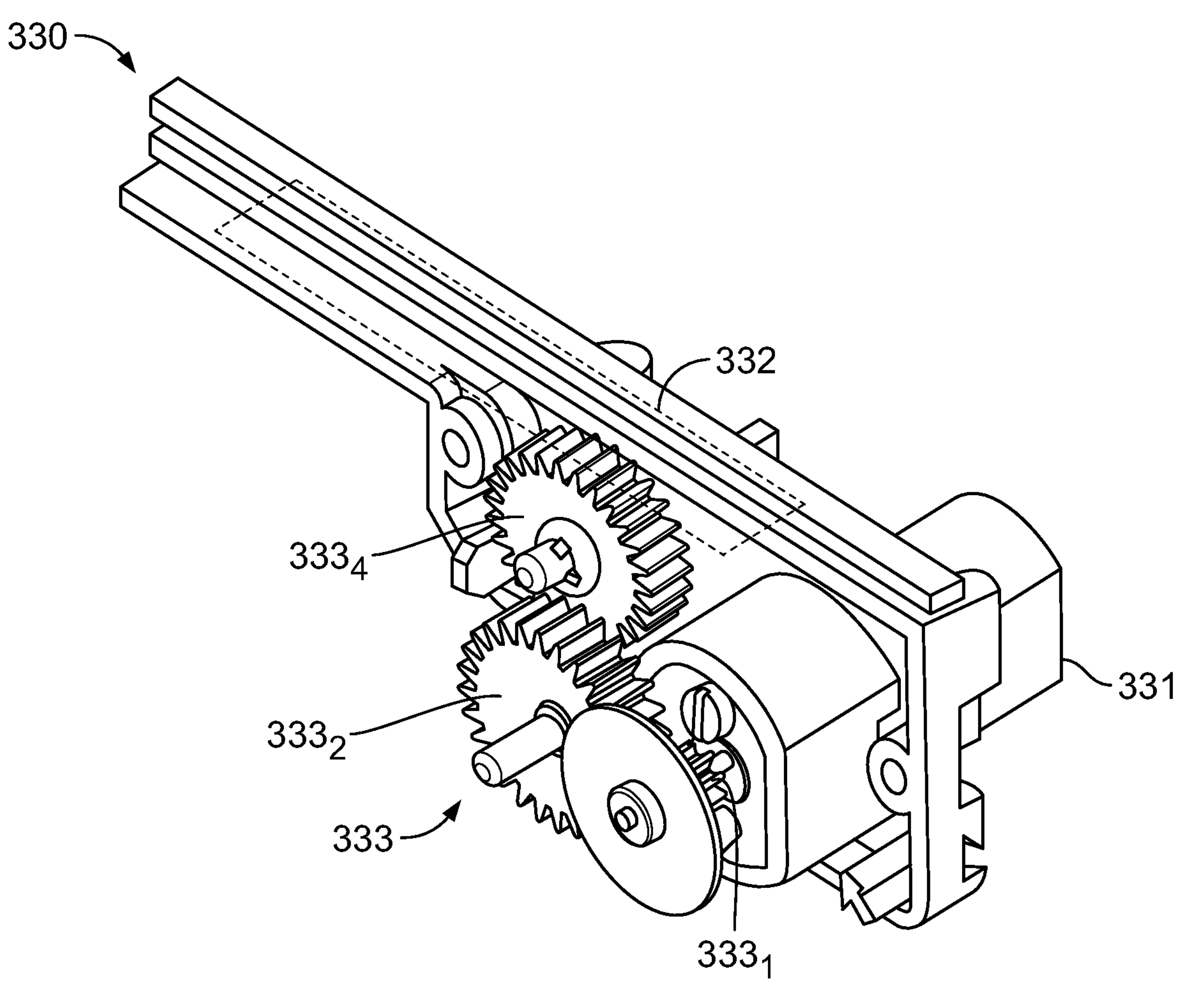
FIG. 30 is a top down perspective side view of an example motorized insertion drive 330 for the autoinjector of FIG. 1.
Figure 31:
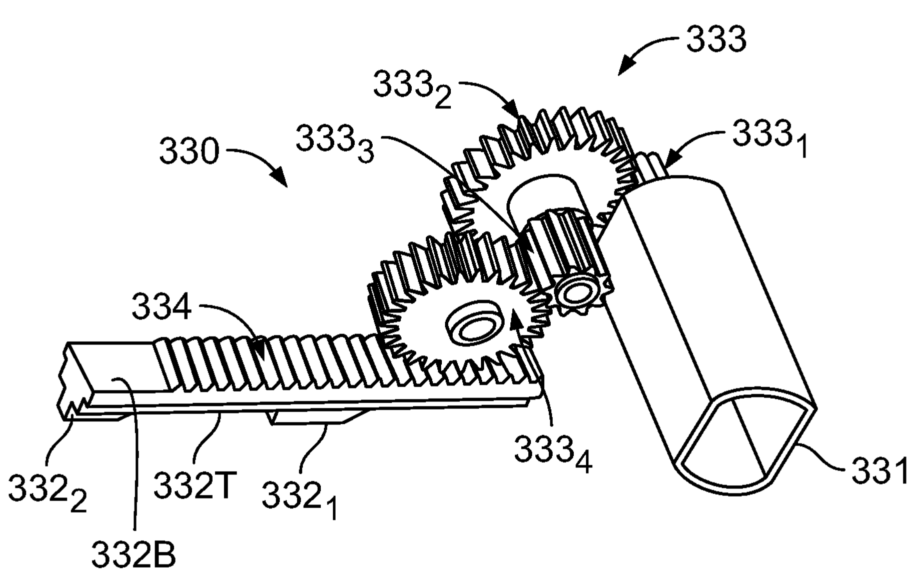
FIG. 31 is a bottom up perspective view of the motorized insertion drive of FIG. 30.

Referring again to FIG. 29, the motorized insertion drive 330 performs a needle insertion cycle and a needle retraction cycle. FIGS. 30 and 31 respectively illustrate a top down perspective side view and a bottom up perspective side view of an embodiment of the motorized insertion drive 330. The insertion drive 300 may comprise an insertion drive motor 331, a drive link or rack 332, and an insertion drive gear train 333 including a plurality of gears 3331, 3332, 3333, 3334, for transmitting the rotary motion of the insertion drive motor 331 to drive the rack 332. The rack 332 may include a top surface 332T and a bottom surface 332B. The top surface 332T of the rack 332 may include spaced-apart first and second protrusions, 3321 and 3322, respectively. The bottom surface 332B of the rack 332 may include rack teeth 334. The rack teeth 334 of the rack engage gear 3334 of the gear train 333. During a needle insertion cycle, the first protrusion 3321 of the rack 332 unlatches the inner sleeve pin 268 of the inner sleeve 220 of the cassette 200 from the latch 218 of the outer cassette housing 210 (FIG. 22) and then engages and then pushes the inner sleeve pin 268 to drive the inner sleeve 220 containing the syringe 260 forward within the outer housing of the cassette 200 from the home position to the needle extended position where the injection needle 265 of the syringe 260 extends out from the cassette 200 and is inserted into the skin at the injection site. During a needle retraction cycle, the second protrusion 3322 of the rack 332 engages and then pulls the inner sleeve pin 268 to drive the inner sleeve 220 containing the syringe 260 backward within the outer housing of the cassette 200 into the home position again, thereby withdrawing the injection needle 265 of the syringe 260 from the skin at the injection site and retracting it back into the cassette 200 (after drug extrusion) where the needle is shielded and locked within the cassette 200 for safe handling and disposal. The needle insertion positioning and timing are monitored and controlled by the microprocessor 350 of the autoinjector. If an error occurs, the error will be indicated on the user interface 312 (FIG. 23) along with audible alert from the speaker. The insertion drive 330 enables the autoinjector apparatus 100 to deliver the pharmaceutical product subcutaneously (SC) with a predetermined needle injection depth. This needle-depth parameter is accomplished when the insertion drive 330 moves the inner sleeve 220/syringe 260 forward to a mechanical hard stop within the outer housing 210 of the cassette 200. The mechanical hard stop limits the travel of the syringe 260 in the direction of the patient's skin, ensuring needle depth to the desired predetermined specification. Monitoring the movement of the motor 331 enables detection of incomplete needle insertion, which will trigger needle retraction and termination of the injection cycle, accompanied by audible and visual alerts.

Figure 32:
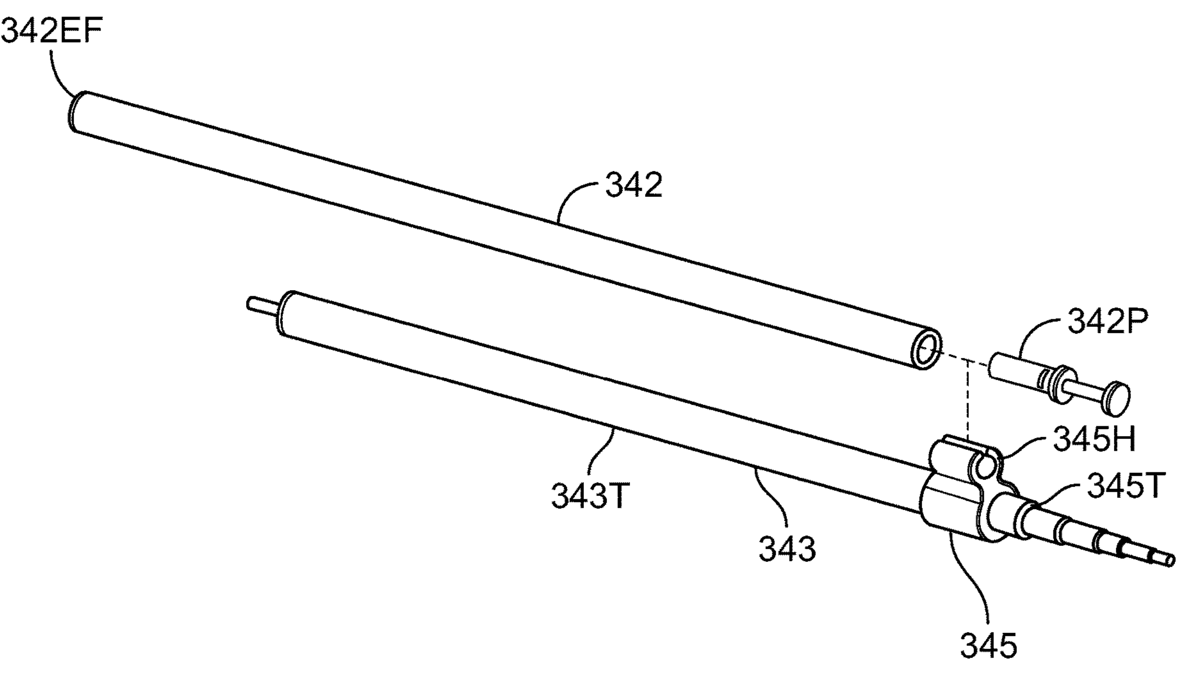
FIG. 32 is an exploded perspective side view of a plunger rod, a lead screw, and a nut of the motorized extrusion drive for the autoinjector of FIG. 1.
Figure 33:
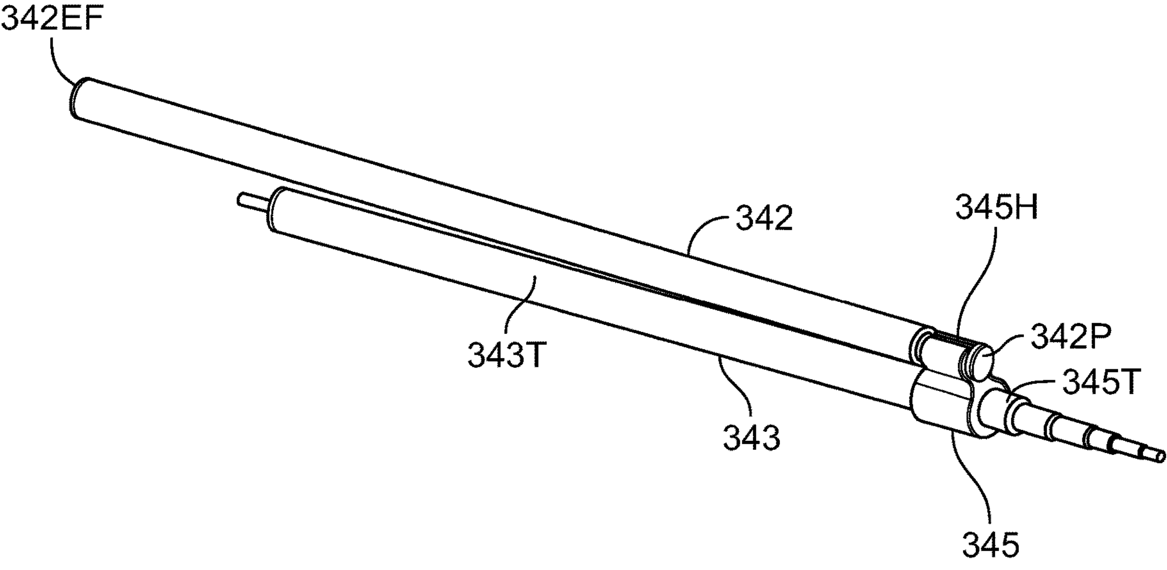
FIG. 33 is an assembled perspective side view of the plunger rod, the lead screw, and the nut of FIG. 32.
Figure 34:
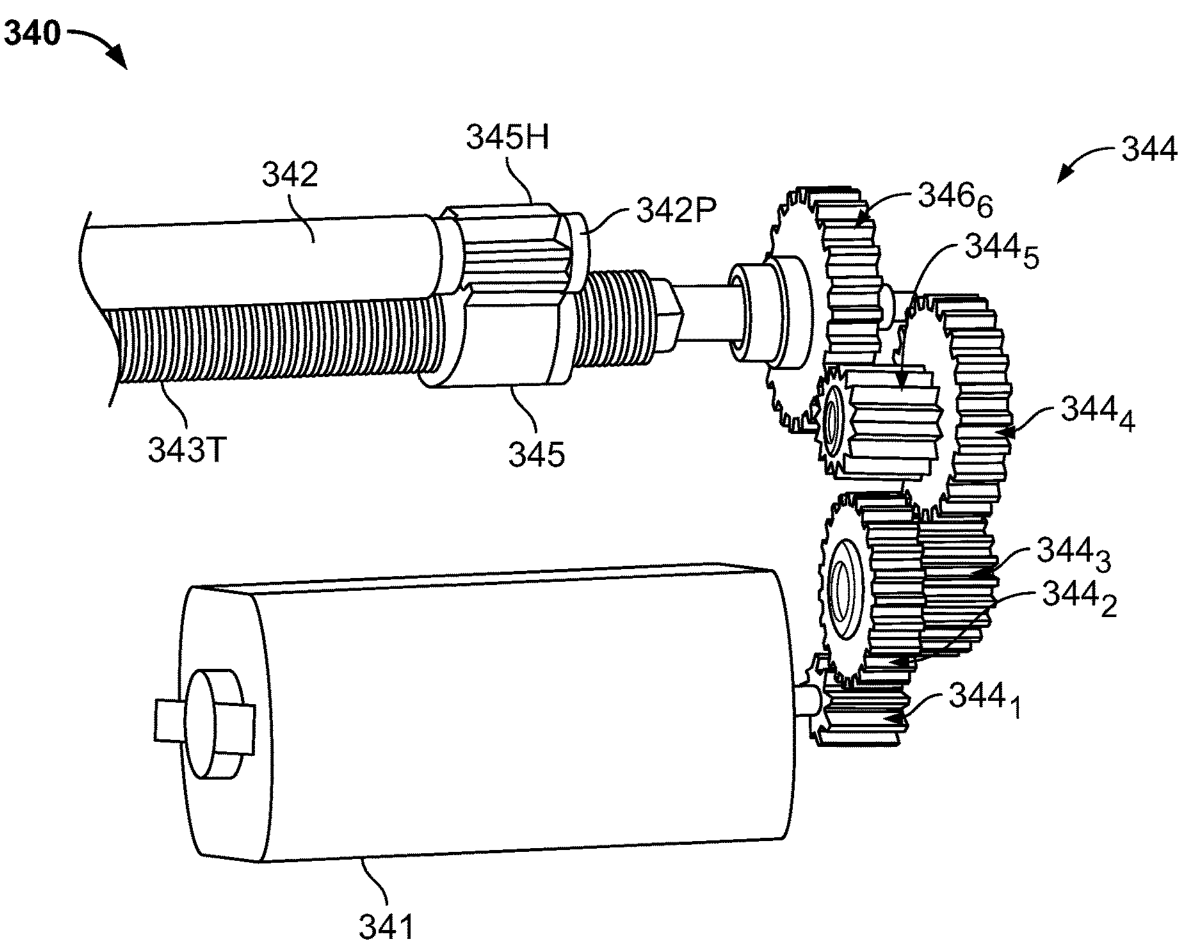
FIG. 34 is a perspective view of a portion of the motorized extrusion drive of FIGS. 30-33.

The motorized extrusion drive 340 illustrated in FIG. 29, performs the drug extrusion cycle where the pharmaceutical product is emptied from the syringe 260. FIGS. 32 and 33 are perspective side views illustrating an embodiment of the motorized extrusion drive 340. FIG. 32 illustrates an exploded perspective side view of an embodiment of a plunger rod/drive screw arrangement of the motorized extrusion drive 340. FIG. 33 illustrates an assembled perspective side view of the plunger rod/drive screw arrangement illustrated in FIG. 32. FIG. 34 illustrates a perspective view of an embodiment of a gear train of the motorized insertion drive 330. The extrusion drive 340 may comprise an extrusion drive motor 341, a plunger rod 342, a lead screw 343, and an extrusion drive gear train 344. The plunger rod 342 is driven by the extrusion drive motor 341 through the lead screw 343 and the extrusion drive gear train 344. As illustrated in FIGS. 32 and 33, the plunger rod 342 may include a pusher 342P and the lead screw 343 may include a nut 345. The nut 345 mechanically couples the plunger rod 342 to the lead screw 343. The nut 345 may include an internal screw thread 345T that threadedly engages an external screw thread 343T of the lead screw 343. The nut 35 may also include a holder 345H that fixedly holds the pusher 342P of the plunger rod 342. As illustrated in FIG. 34, the extrusion drive gear train 344 may include a plurality of gears 3441, 3442, 3443, 3444, 3445, 3446. The gears 3441 and 3446 of the extrusion drive gear train 344 are coupled to the extrusion drive motor 341 and the lead screw 343, respectively, thereby allowing the extrusion drive gear train 344 to transmit the rotary motion of the insertion drive motor 331 to drive the lead screw 343. As the lead screw 343 rotates, the nut 345 (which is threadedly engaged with the lead screw 343) moves forward or backward (depending upon the lead screw's direction of rotation) along the lead screw 343, which in turn, drives the plunger rod 342 forward and backward in the autoinjector 300. Forward movement of the plunger rod 342 causes an end face 342EF of the plunger rod 342 to enter the cassette 200 and subsequently the syringe barrel 261 of the syringe 260. The plunger rod 343 then engages the plunger-stopper 264 of the syringe 260 and pushes it to the end of the syringe barrel 261 in order to expel the predetermined dose of the pharmaceutical product from the syringe 260 during a drug extrusion cycle. The position of the components of extrusion drive 340, as well as time related to drug extrusion, may be monitored by the microprocessor 350. If an error occurs, the error can be indicated on the user interface 312 along with an audible alert. The microprocessor 350 may be capable of storing different factory-set drug delivery profiles (stroke, speed, acceleration). A plurality of unique drug delivery profiles may be associated with specific cassette configurations. The cassette identification arrangement on the outer housing 210 of the cassette 200 enable the autoinjector 300 to identify the proper drug delivery profile specific for the loaded pharmaceutical product. Upon insertion and recognition of a valid cassette 200, available preset drug extrusion speed ranges may be automatically registered by the autoinjector 300. Available speed ranges are dependent upon the syringe fill volume and pharmaceutical product characteristics, such as viscosity.

The user may select the desired drug extrusion speed (defined as the time to empty the pharmaceutical product of the syringe 260) from a plurality of different options for a particular pharmaceutical product using the speed selector switch 316. Upon initiation of the drug extrusion cycle, the stroke of the plunger rod 342 may be controlled and monitored to ensure the plunger-stopper 264 reaches the end of the syringe barrel 261, which ensures complete dose administration. If an error occurs during the extrusion process (e.g., failure of the plunger rod to achieve a complete stroke), the autoinjector 300 may immediately terminate drug extrusion, retract the needle back into the cassette 200, and provide audible and visual alerts.

The injection cycles may be indicated by both audible and visual signals. Lights on the autoinjector 300 may turn off in sequence from top to bottom during the injection cycle to indicate to the user the progress of the injection. Upon completion of the injection cycle, the autoinjector 300 retracts the syringe needle back into the disposable cassette 200, and then opens the cassette door 308 automatically, allowing removal of the cassette 200 by the user. The opening of the cassette door 308 may also be an indicator to the user that the injection cycle is complete.

In the event that an error occurs during the injection cycle, the autoinjector 300 may be equipped with various audible and visual signals to alert the user (operator or patient) to the error and to prompt appropriate actions.

The battery 360 illustrated in FIG. 29, may be a non-replaceable, non-rechargeable battery. In other forms, the battery 360 can be a replaceable battery and/or a rechargeable battery. The battery 360 should be capable of providing sufficient power for adequate shelf-life and service life to meet the drug delivery requirements. A power-on self-test is automatically performed upon waking the autoinjector 300 to ensure sufficient battery power is available for a successful injection cycle. The user interface 312 of the autoinjector 300 may provide visual and audible alerts if a problem occurs with the battery 360 before injection. The microprocessor 350 may be programmed to disable the autoinjector 300 at the end of the defined service life or if the battery 360 is not sufficiently charged for a successful injection cycle.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like;Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4I37 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/Ilia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-a4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-a581 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MY0-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s)

disclosed herein, and that such modifications, alterations, and combinations are to be viewed as being within the ambit of the inventive concept(s).

What is claimed is:

1. A cassette fer a drug delivery device, the cassette comprising:
 a housing:
 a drive mechanism disposed at least partially within the housing and comprising a plunger rod configured to move relative to the housing during a drug extrusion operation; and
 a cassette comprising:
  a sleeve having a proximal end and a distal end;
  a syringe disposed in the sleeve, the syringe comprising a barrel having a distal opening adjacent to the distal end of the sleeve;
  a plunger-stopper slidably disposed within the barrel;
  an end cap coupled to the distal end of the sleeve adjacent the distal opening of the barrel to secure the syringe in the sleeve; and
  a spacer disposed distally of the plunger-stopper having a diameter approximately equal to a diameter of the plunger-stopper, the spacer configured and sized to be slidably moved within the barrel and adapted to be engaged by the plunger rod of the drive mechanism to slide within the barrel and engage the plunger-stopper, wherein, following assembly of the cassette within the housing and until the drug extrusion operation, the spacer is spaced from the plunger-stopper by a gap, and wherein the spacer is brought into initial contact with the plunger-stopper by movement of the plunger rod when the plunger rod moves to expel a drug from the syringe during the drug extrusion operation.

2. The drug delivery device of claim 1, wherein the spacer is disposed between the plunger-stopper and the end cap.

3. The drug delivery device of claim 1, wherein the spacer is disposed adjacent to the distal end of the barrel.

4. The drug delivery device of claim 1, where the end cap secures the spacer to the barrel prior to drug delivery.

5. The drug delivery device of claim 1, wherein the spacer comprises a cup-shaped body having a rearwardly opening cavity sized to receive a plunger rod therein, wherein the body further optionally comprises a plurality of ribs extending inwardly within the cavity.

6. The drug delivery device of claim 1, wherein the spacer is sized to frictionally engage an interior surface of the barrel to resist mass forces.

7. The drug delivery device of claim 1, wherein the spacer comprises a vent allowing air to flow past the spacer as the spacer is moved along the barrel, wherein the vent optionally comprises either (a) or (b), as follows:
 (a) a plurality of passages extending between radial protrusions arrayed around a circumference of the spacer, or
 (b) one or more longitudinal channels recessed within an outer surface of the spacer.

8. The drug delivery device of claim 1, wherein, following the assembly of the cassette within the housing and until the drug extrusion operation, the spacer is spaced from the plunger-stopper by the gap and engages the plunger rod.

9. The drug delivery device of claim 1, wherein the end cap comprises an interior breakaway portion, and the spacer is secured to the breakaway portion, wherein the spacer is optionally molded over the breakaway portion.

10. The drug delivery device of claim 9, wherein the breakaway portion comprises a disc, and an end wall of the spacer is molded over the disc.

11. The drug delivery device of claim 9, wherein the breakaway portion further comprises a side wall extending rearwardly from edges of the disc.

12. The drug delivery device of claim 9, wherein the sleeve comprises at least one receptacle, and the end cap comprises an elastomeric bumper adapted to contact a distal end of the syringe and at least one arm member for inserting into the at least one receptacle.

13. The drug delivery device of claim 9, further comprising a therapeutic product in the syringe.

14. The drug delivery device of claim 13, wherein the therapeutic product is Epogen®, Aranesp®, Enbrel® Neulasta®, Neupogen®, Nplate®, Vectibix®, Sensipar®, Xgeva®, Prolia®, an antibody to IL-17 Receptor A, antagonist of angiopoietin-2, a TNF blocker or inhibitor, etanercept, adalimumab, certolizumab, golimumab or infliximab.

15. A method comprising:
 providing an autoinjector comprising: a housing, and a drive mechanism disposed at least partially within the housing and comprising a plunger rod configured to move relative to the housing during a drug extrusion operation;
 providing a cassette comprising:
  a plunger-stopper disposed within a barrel of a syringe; the syringe being disposed within a sleeve;
  a spacer sized to be slidably received within the barrel rearwardly from the plunger-stopper, wherein the spacer is brought into initial contact with the plunger-stopper by movement of the plunger rod of the autoinjector when the plunger rod moves to expel a drug from the syringe during the drug extrusion operation; and
  an end cap coupled to the sleeve to secure the syringe in the sleeve; and
 assembling the cassette within a housing of the autoinjector such that, following the assembly of the cassette within the housing of the autoinjector and until the drug extrusion operation, the spacer is spaced from the plunger-stopper by a gap.

16. The method of claim 15, wherein mounting the spacer rearwardly from the plunger-stopper comprises disposing the spacer in the barrel of the syringe rearward of the plunger-stopper.

17. The method of claim 15, wherein mounting the spacer rearwardly from the plunger-stopper comprises coupling the spacer to the end cap, such that coupling the end cap to the sleeve aligns the spacer with the barrel.

18. The method of claim 17, wherein coupling the spacer to the end cap for the sleeve comprises molding the spacer over a breakaway portion of the end cap.

19. The method of claim 15, further comprising filling the syringe with a therapeutic product.

20. The method of claim 15, further comprising receiving a plunger rod of the autoinjector in a rearwardly open cavity of the spacer for the plunger rod to drive the spacer through the barrel to engage the plunger-stopper.

21. The method of claim 15, further comprising selecting the spacer from a plurality of available spacers, each of the plurality of available spacers having distinct dimensions.

22. The method of claim 15, following the assembly of the cassette within the housing and until the drug extrusion operation, the spacer is spaced from the plunger-stopper by the gap and engages the plunger rod.

* * * * *